(12) United States Patent
Cardon et al.

(10) Patent No.: US 11,464,645 B2
(45) Date of Patent: Oct. 11, 2022

(54) SET FOR A GLENOID IMPLANT

(71) Applicant: Tornier, Montbonnot-Saint-Martin (FR)

(72) Inventors: Jean-Emmanuel Cardon, Domene (FR); Benjamin Dassonville, Saint Hilaire du Touvet (FR); Christophe Magnac, Revel (FR)

(73) Assignee: TORNIER, Montbonnot-Saint-Martin (FR)

( * ) Notice: Subject to any disclaimer, the term of this patent is extended or adjusted under 35 U.S.C. 154(b) by 0 days.

(21) Appl. No.: 16/519,937

(22) Filed: Jul. 23, 2019

(65) Prior Publication Data
US 2019/0343643 A1 Nov. 14, 2019

Related U.S. Application Data
(63) Continuation of application No. 15/625,017, filed on Jun. 16, 2017, now Pat. No. 10,426,625.

(30) Foreign Application Priority Data

Jun. 24, 2016 (EP) .................................... 16305767

(51) Int. Cl.
*A61F 2/40* (2006.01)
*A61B 17/86* (2006.01)
(Continued)

(52) U.S. Cl.
CPC ........ *A61F 2/4081* (2013.01); *A61B 17/8605* (2013.01); *A61B 17/8625* (2013.01);
(Continued)

(58) Field of Classification Search
CPC ....... A61F 2/40–4081; A61F 2002/4007–4096
See application file for complete search history.

(56) References Cited

U.S. PATENT DOCUMENTS

| 5,489,309 A | 2/1996 | Lackey et al. |
| 6,063,124 A | 5/2000 | Amstutz |
| (Continued) | | |

FOREIGN PATENT DOCUMENTS

| EP | 1 639 967 | 3/2006 |
| EP | 1 952 788 | 8/2008 |
| (Continued) | | |

OTHER PUBLICATIONS

European Search Report issued in EP Application No. 16305767, dated Jan. 10, 2017, in 7 pages.
(Continued)

*Primary Examiner* — Brian A Dukert
*Assistant Examiner* — Rebecca Lynee Zimmerman
(74) *Attorney, Agent, or Firm* — Duane Morris LLP

(57) ABSTRACT

This set comprising:
an anatomic articulating member, having a concave articulating surface intended to articulate with a complementary humeral implant and having an anatomic coupling feature,
a reversed articulating member, having a convex articulating surface intended to articulate with a complementary humeral implant and having a reversed coupling feature that is shaped differently from the anatomic coupling feature, and
an anchorage member intended to be anchored in a human glenoid, the anchorage member including a body which defines a proximodistal axis and has inner bore extending along the proximodistal axis, the body being provided within the inner bore with both an inner first feature that is designed to cooperate with the anatomic coupling feature when the anatomic coupling feature is introduced within the inner bore, so as to fixedly couple the anchorage member with the anatomic articulating
(Continued)

member, and an inner second feature that is designed to cooperate with the reversed coupling feature when the reversed coupling feature is introduced within the inner bore, so as to fixedly couple the anchorage member with the reversed articulating member, the first feature and the second feature being distinct from each other. The body is operable to be axially introduced into the glenoid before being coupled indifferently with one or the other of the anatomic and reversed articulating members.

20 Claims, 18 Drawing Sheets

(51) Int. Cl.
*A61F 2/28* (2006.01)
*A61F 2/30* (2006.01)

(52) U.S. Cl.
CPC ............ *A61F 2/28* (2013.01); *A61F 2/30724* (2013.01); *A61F 2002/2835* (2013.01); *A61F 2002/30062* (2013.01); *A61F 2002/3079* (2013.01); *A61F 2002/30245* (2013.01); *A61F 2002/30289* (2013.01); *A61F 2002/30405* (2013.01); *A61F 2002/30433* (2013.01); *A61F 2002/30774* (2013.01); *A61F 2002/30892* (2013.01); *A61F 2002/30901* (2013.01); *A61F 2002/4085* (2013.01)

(56) References Cited

U.S. PATENT DOCUMENTS

| | | | |
|---|---|---|---|
| 6,666,874 B2 * | 12/2003 | Heitzmann | A61B 17/320758 |
| | | | 606/159 |
| 7,204,854 B2 | 4/2007 | Guederian et al. | |
| 7,208,222 B2 | 4/2007 | Rolfe et al. | |
| 8,641,773 B2 | 2/2014 | Bergin et al. | |
| 8,864,834 B2 | 10/2014 | Boileau et al. | |
| 9,498,345 B2 * | 11/2016 | Burkhead, Jr. | A61F 2/4081 |
| 10,426,625 B2 | 10/2019 | Cardon et al. | |
| 11,229,524 B2 | 1/2022 | Sperling et al. | |
| 2001/0034553 A1 | 10/2001 | Michelson | |
| 2003/0114933 A1 | 6/2003 | Bouttens et al. | |
| 2004/0049270 A1 | 3/2004 | Gerwitz | |
| 2004/0220674 A1 * | 11/2004 | Pria | A61F 2/40 |
| | | | 623/19.12 |
| 2004/0254646 A1 | 12/2004 | Stone et al. | |
| 2005/0267478 A1 | 12/2005 | Corradi et al. | |
| 2006/0009852 A1 | 1/2006 | Winslow et al. | |
| 2006/0020344 A1 | 1/2006 | Shultz et al. | |
| 2006/0064173 A1 | 3/2006 | Guederian | |
| 2006/0142866 A1 | 6/2006 | Baratz et al. | |
| 2007/0156246 A1 | 7/2007 | Meswania et al. | |
| 2007/0173945 A1 | 7/2007 | Wiley et al. | |
| 2007/0225817 A1 * | 9/2007 | Reubelt | A61B 17/1684 |
| | | | 623/19.11 |
| 2009/0281630 A1 | 11/2009 | Delince et al. | |
| 2011/0153023 A1 | 6/2011 | Deffenbaugh et al. | |
| 2011/0224673 A1 | 9/2011 | Smith | |
| 2012/0022664 A1 | 1/2012 | Vandermeulen et al. | |
| 2012/0184964 A1 | 7/2012 | Hudak, Jr. | |
| 2012/0221111 A1 | 8/2012 | Burkhead, Jr. et al. | |
| 2012/0253467 A1 * | 10/2012 | Frankle | A61F 2/4059 |
| | | | 623/19.11 |
| 2012/0277880 A1 * | 11/2012 | Winslow | A61F 2/4081 |
| | | | 623/19.11 |
| 2013/0018476 A1 | 1/2013 | Katrana et al. | |
| 2013/0123929 A1 * | 5/2013 | McDaniel | A61F 2/40 |
| | | | 623/19.13 |
| 2013/0150972 A1 | 6/2013 | Iannotti et al. | |
| 2013/0261629 A1 | 10/2013 | Anthony et al. | |
| 2013/0261754 A1 | 10/2013 | Anthony et al. | |
| 2013/0282129 A1 | 10/2013 | Phipps | |
| 2014/0074246 A1 | 3/2014 | Huebner et al. | |
| 2014/0236304 A1 | 8/2014 | Hodorek et al. | |
| 2014/0257499 A1 | 9/2014 | Winslow et al. | |
| 2015/0134066 A1 | 5/2015 | Bachmaier | |
| 2015/0250601 A1 | 9/2015 | Humphrey | |
| 2015/0289984 A1 | 10/2015 | Budge | |
| 2016/0324648 A1 | 11/2016 | Hodorek et al. | |
| 2017/0304063 A1 | 10/2017 | Hatzidakis et al. | |
| 2018/0064537 A1 * | 3/2018 | Pressacco | A61F 2/4081 |

FOREIGN PATENT DOCUMENTS

| | | | |
|---|---|---|---|
| EP | 2586387 A1 | | 5/2013 |
| JP | 2009523578 A | | 6/2009 |
| WO | 2016094739 A1 | | 6/2016 |
| WO | WO2016094739 A1 | | 6/2016 |

OTHER PUBLICATIONS

Neyton et al., "Glenoid Bone Grafting with a Reverse Design Prosthesis", *Journal of Shoulder and Elbow Surgery*, 2007, vol. 16, Issue 3, Supplement, May-Jun. 2007, pp. S71-S78.
Final Rejection issued in connection with U.S. Appl. No. 17/250,964, dated Jul. 26, 2021, 22 pages.
Non-Final Office Action issued in connection with U.S. Appl. No. 17/250,964, dated Jul. 26, 2021, 27 pages.
Final Rejection issued in connection with U.S. Appl. No. 16/249,720, dated Aug. 20, 2021, 40 pages.
Final Rejection issued in connection with U.S. Appl. No. 16/580,367, dated Aug. 24, 2021, 9 pages.
First Office Action issued in connection with Japanese Patent Application No. 2019-555151, dated Feb. 21, 2022, 5 pages.
Non-Final Office Action issued in connection with U.S. Appl. No. 17/250,964, dated Feb. 24, 2022, 12 pages.
Non-Final Office Action issued in connection with U.S. Appl. No. 16/648,128, filed Mar. 28, 2022, 43 pages.
Office Action issued in connection with Japanese Patent Application No. 2021-518159, dated May 24, 2022, 5 pages.
Third Examination Report issued in connection with Australian Patent Application No. 2019355854, dated May 10, 2022, 4 pages.
First Examination Report issued in connection with Australian Patent Application No. 2021250994, dated Jun. 2, 2022, 5 pages.

* cited by examiner

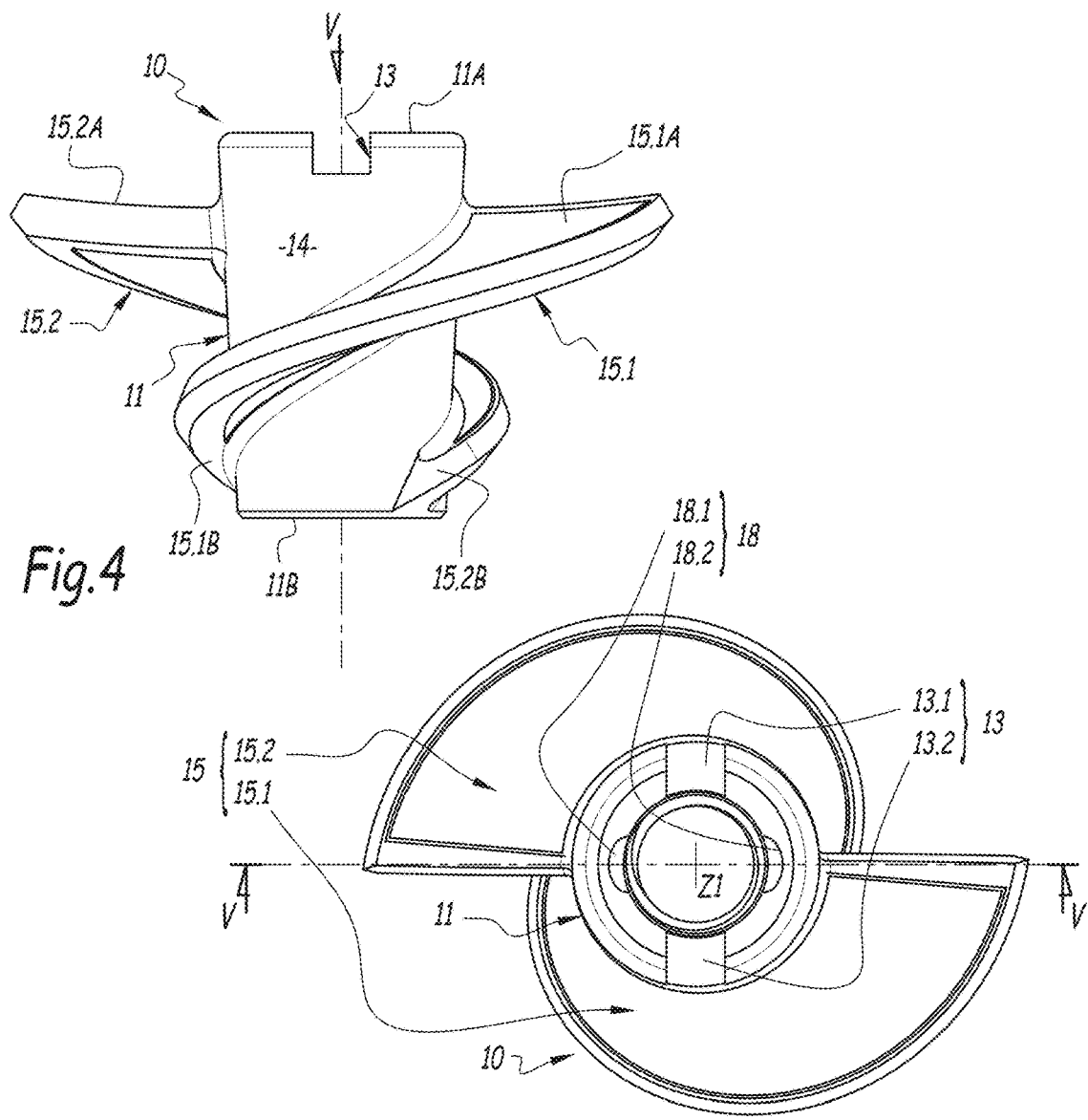
Fig.4
Fig.5
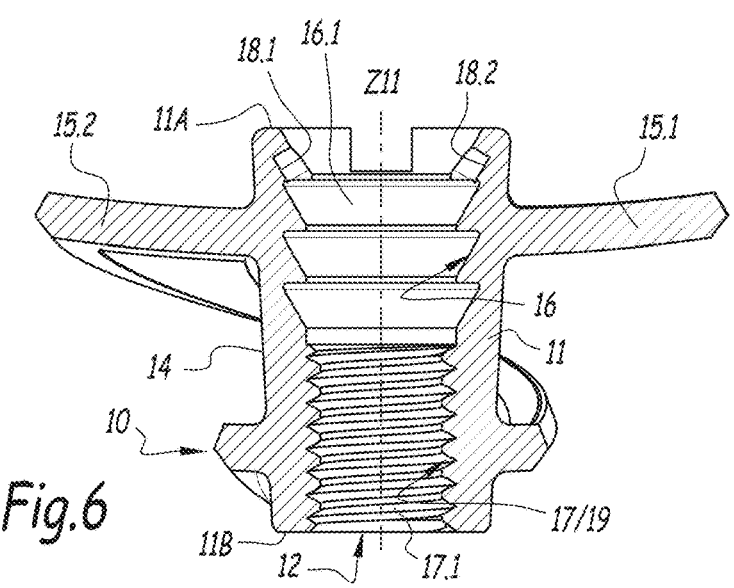
Fig.6

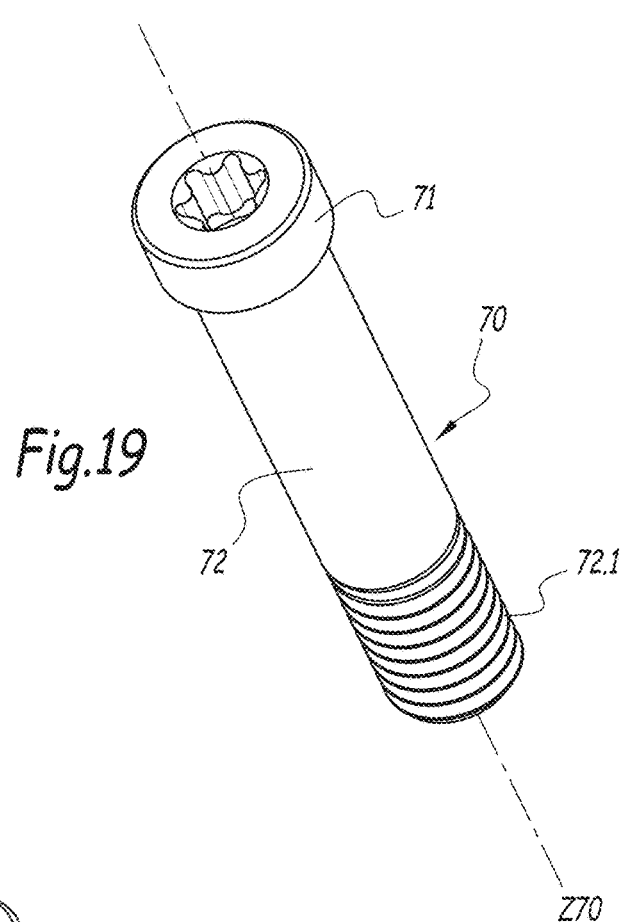
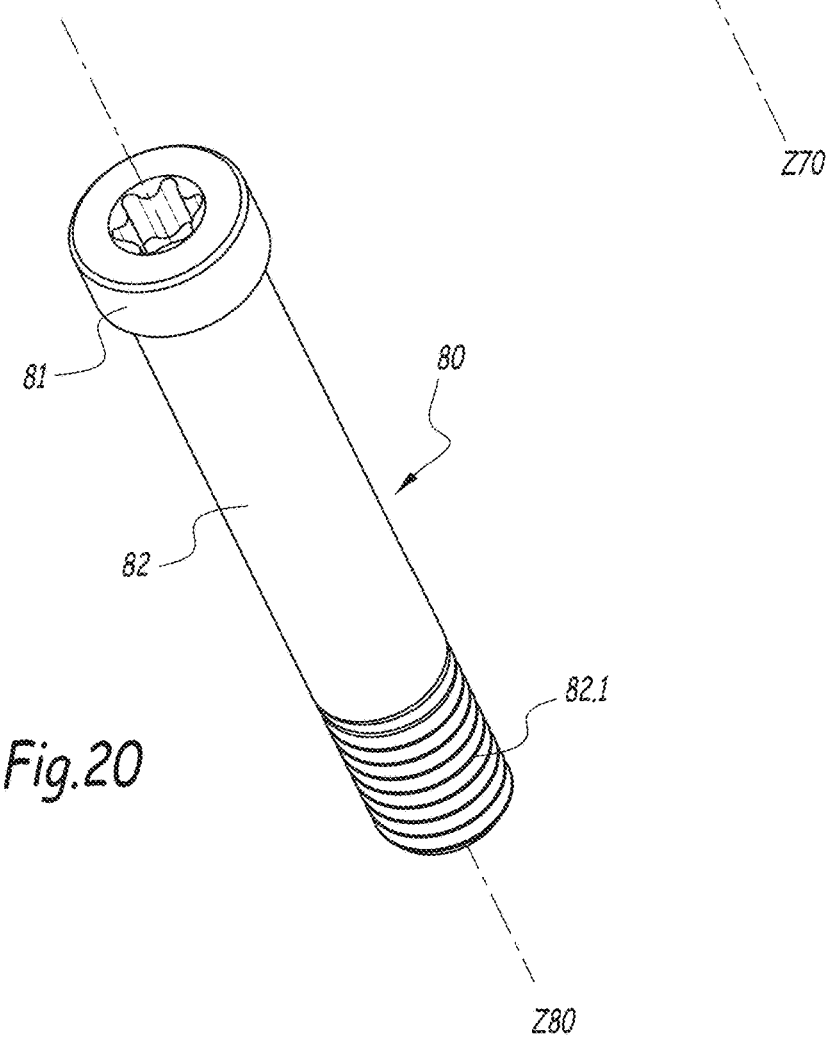

SET FOR A GLENOID IMPLANT

The present invention relates to a set for a glenoid implant. The invention also relates to glenoid implants.

In a healthy human shoulder, the head of the humerus, which is generally ball-shaped, and the glenoid cavity of the scapula, articulate with each other and form a ball-and-socket joint. Total shoulder arthroplasty is a common treatment for shoulder pain resulting from arthritis or injury and leads to replace the ball-and-socket joint by a shoulder orthopedic prosthesis comprising both a glenoid implant to be implanted on the glenoid of the scapula and a humeral implant to be implanted on the humerus. A shoulder prosthesis is considered as being anatomic when the glenoid implant has a concave articulating surface with which a complementary convex surface of the humeral implant articulates. A shoulder prosthesis is considered as being reversed when the glenoid implant has a convex articulating surface with which a complementary concave surface of the humeral implant articulates, the natural anatomy of the ball-and-socket joint of the shoulder thus being reversed.

For some patients, the anatomic shoulder prosthesis is often used in primary replacement and the reversed shoulder prosthesis can then be used when a revision is necessary. For other patients, the reversed shoulder prosthesis is directly implanted. Choosing the anatomic or the reversed shoulder prosthesis is made by the surgeon, if appropriate during surgery, and depends on various factors including, amongst others, quantity and quality of the bone tissue of the glenoid of the patient's scapula. There is needed, therefore, a set of glenoid implants allowing to implant indifferently an anatomic shoulder prosthesis and a reversed shoulder prosthesis or even to convert an anatomic shoulder prosthesis to a reversed shoulder prosthesis.

Besides, for some patients, the bone loss of their glenoid can be great. Adding a bone graft to the glenoid implant of the shoulder prosthesis may be necessary. For that reason, there is needed a glenoid implant which makes easier to selectively incorporate such a bone graft.

Furthermore, there is a constant need to strengthen the attachment of the glenoid implant to the glenoid of the scapula, but without leading to dissociate an articulating part of the glenoid implant from another part that is directly engaged with the glenoid.

One of the goals of the present invention is to overcome at least some of the aforementioned problems.

To this end, one object of the invention is a set for a glenoid implant, comprising:
  an anatomic articulating member, having a concave articulating surface intended to articulate with a complementary humeral implant and having an anatomic coupling feature,
  a reversed articulating member, having a convex articulating surface intended to articulate with a complementary humeral implant and having a reversed coupling feature that is shaped differently from the anatomic coupling feature, and
  an anchorage member intended to be anchored in a human glenoid, the anchorage member including a body which defines a proximodistal axis and has an inner bore extending along the proximodistal axis, the body being provided within the inner bore with both an inner first feature that is designed to cooperate with the anatomic coupling feature when the anatomic coupling feature is introduced within the inner bore, so as to fixedly couple the anchorage member with the anatomic articulating member, and an inner second feature that is designed to cooperate with the reversed coupling feature when the reversed coupling feature is introduced within the inner bore, so as to fixedly couple the anchorage member with the reversed articulating member, the first feature and the second feature being distinct from each other,
  the body being operable to be axially introduced into the glenoid before being coupled indifferently with one or the other of the anatomic and reversed articulating members.

The set according to the invention allows implanting a glenoid implant indifferently for an anatomic shoulder prosthesis and for a reversed shoulder prosthesis, by using easily and safely a same member for anchoring in the glenoid of a patient. This anchorage member can be left in place in the glenoid when converting the glenoid implant from an anatomic configuration to a reversed configuration.

According to additional advantageous features of this set:
  The first feature and the second feature are located at respective axial levels of the body that are different from each other.
  The anatomic coupling feature and the first feature cooperate with each other by fitting along the proximodistal axis.
  The anatomic coupling feature and the first feature are fitted together by snap fit along the proximodistal axis.
  The first feature comprises a corrugated hole that is centered on the proximodistal axis, and the anatomic coupling feature comprises a peg that is integral with an insert of the anatomic articulating member and that is shaped to be axially received and to be wedged in the corrugated hole.
  The reversed coupling feature and the second feature cooperate with each other by a screw connection.
  The second feature comprises a threaded hole that is centered on the proximodistal axis, and the reversed coupling feature comprises a coupling screw including a head that is axially engaged with a baseplate of the reversed articulating member and a rod that is threaded to be screwed into the threaded hole.
  The anatomic articulated member comprises an insert having a proximal face, on which is formed the concave articulating surface, and a distal face, from which at least a part of the anatomical coupling feature protrudes.
  The reversed articulating member comprises a glenosphere, on which is formed the convex articulating surface, and a baseplate having a proximal face, on which the glenosphere is fixedly mounted, and a distal face from which at least a part of the reversed coupling feature protrudes.
  The glenosphere is fixedly mounted on the baseplate by a taper connection that is centered on the proximodistal axis.
  The glenosphere defines a central axis which is both parallel to the proximodistal axis and offset from the proximodistal axis when the reversed articulating member is coupled with the anchorage member.
  The set further comprises:
    a spacer which is operable to be axially interposed between the body and one or the other of the anatomic articulating member and the reversed articulating member when the anchorage member is coupled indifferently with one or the other of the anatomic and reversed articulating members, and
    a bone graft which is conformed to surround the spacer and to be arranged axially between the glenoid and one or the other of the anatomic articulating member and the reversed articulating member.

The body is provided with an outer thread which is designed, when the body is driven in rotation around the proximodistal axis so as to be introduced into the glenoid, to pass through a subchondral bone layer of the glenoid by entirely passing from above to below the subchondral bone layer so that a proximal end of the thread engages an underside of the subchondral bone layer and the rest of the thread enters spongious bone of the glenoid.

The body is provided with an outer thread which is designed, when the body is driven in rotation around the proximodistal axis so as to be introduced into the glenoid, to pass through a subchondral bone layer of the glenoid, the outer thread including at least one portion of helix which has a lead between twelve and eighteen millimeters and wraps around the body over less than one turn and more than half of one turn.

The set further comprises a bone fastening screw intended to be screwed into cortical bone of the glenoid, the bone fastening screw being operable to be axially passed through the body so that a threaded rod of the bone fastening screw protrudes axially from the body so as to be screwed into cortical bone of the glenoid while a threaded head of the bone fastening screw is screwed in a complementary threaded distal hole of the body.

Another object of the invention is a first glenoid implant, comprising:
an articulating member intended to articulate with a humeral implant;
an anchorage member intended to be anchored in a human glenoid, the anchorage member including a body which defines a proximodistal axis and which is operable to be axially introduced into the glenoid before being fixedly coupled with the articulating member;
a spacer which is operable to be axially interposed between the body and the articulating member when the body and the articulating member are coupled to each other; and
a bone graft which is conformed to surround the spacer and to be arranged axially between the glenoid and the articulating member.

Thanks to the spacer of this glenoid implant, a bone graft can be easily incorporated in the glenoid implant and the articulating member may be lateralized with respect to the scapula, which has functional interests especially for a reversed shoulder prosthesis.

According to additional advantageous features of this first glenoid implant:
The spacer extends as a coaxial extension of the body.
The spacer is removably attached to the body.
The spacer is clipped on a proximal part of the body.
The spacer is integral with the body.
The articulating member has a coupling feature, the body is provided with an inner feature that is designed to cooperate with the coupling feature to fixedly couple the anchorage member with the articulating member, and the spacer is axially hollow so that the coupling feature freely passes through the spacer to cooperate with the inner feature.
The articulating member is a reversed articulating member having a convex articulating surface intended to articulate with a complementary articulating surface of the humeral implant.
The reversed articulating member comprises a glenosphere, on which is formed the convex articulating surface, and a baseplate on which is fixedly mounted the glenosphere, the bone graft being arranged axially between the glenoid and the baseplate.
The reversed articulating member further comprises a coupling screw for fixedly coupling the baseplate with the body, the coupling screw including:
a head that is axially engaged with the baseplate, and
a rod that is threaded to be screwed into a threaded hole of the body after being freely passed through the spacer.

The bone graft is selected from the group consisting of autologous graft, allograft and synthetic graft.

Another object of the invention is a second glenoid implant, comprising:
an articulating member intended to articulate with a humeral implant, and
an anchorage member intended to be anchored in a human glenoid, the anchorage member including a body which defines a proximodistal axis and which is operable to be axially introduced into the glenoid before being fixedly coupled with the articulating member,
the body being provided with an outer thread which is designed, when the body is driven in rotation around the proximodistal axis so as to be introduced into the glenoid, to pass through a subchondral bone layer of the glenoid by entirely passing from above to below the subchondral bone layer so that a proximal end of the thread engages underside of the subchondral bone layer and the rest of the thread enters spongious bone of the glenoid.

In some embodiments, the thread includes at least one portion of helix, which has a proximal end forming the proximal end of the thread and which is designed to entirely pass through the subchondral bone layer via a longitudinal slot of the subchondral bone layer when the body is driven in rotation around the proximodistal axis so as to be introduced into the glenoid. In some embodiments, the at least one portion of helix has a lead between twelve and eighteen millimeters and wraps around the body over less than one turn and more than half of one turn.

Another object is a third glenoid implant, comprising:
an articulating member intended to articulate with a humeral implant, and
an anchorage member intended to be anchored in a human glenoid, the anchorage member including a body which defines a proximodistal axis and which is operable to be axially introduced into the glenoid before being fixedly coupled with the articulating member,
the body is provided with an outer thread which is designed, when the body is driven in rotation around the proximodistal axis so as to be introduced into the glenoid, to pass through a subchondral bone layer of the glenoid, the outer thread including at least one portion of helix which has a lead between twelve and eighteen millimeters and wraps around the body over less than one turn and more than half of one turn.

Thanks to the thread of the second and third glenoid implants, the anchorage member can be screwed into the glenoid so as to place the thread just below the subchondral bone layer of the glenoid. In that way, the subchondral part of the glenoid securely retains the anchorage member into the glenoid, especially without adding cement, and the articulating member of the glenoid implant can be in direct contact either with topside of the subchondral bone layer or with a bone graft covering the subchondral bone layer, so that in use, the stress on the articulating member is essentially applied directly to the subchondral bone layer or to the aforesaid bone graft, instead of being essentially applied to the anchorage member, in order to prevent the release or dissociation thereof with respect to the articulating member.

According to additional advantageous features of the second and third glenoid implants:

- The at least one portion of helix has a width which gradually decreases from its proximal end to its distal end.
- Two portions of helix are provided, which are symmetrical with respect to the proximodistal axis.
- The articulating member has a coupling feature, the body is provided with an inner feature that is designed to cooperate with the coupling feature to fixedly couple the anchorage member with the articulating member so that the articulating member is in direct contact either with topside of the subchondral bone layer or with a bone graft covering the subchondral bone layer.
- The articulating member is an anatomical articulating member having a concave articulating surface intended to articulate with a complementary articulating surface of the humeral implant.
- The articulating member is a reversed articulating member having a convex articulating surface intended to articulate with a complementary articulating surface of the humeral implant.
- The reversed articulating member comprises a glenosphere, on which is formed the convex articulating surface, and a baseplate on which is fixedly mounted the glenosphere, the bone graft being arranged axially between the glenoid and the baseplate.
- The glenosphere is fixedly mounted on the baseplate by a taper connection that is centered on the proximodistal axis.
- A part of the taper connection is integral with the body.
- The glenosphere defines a central axis which is both parallel to the proximodistal axis and offset from the proximodistal axis when the reversed articulating member is coupled with the anchorage member.
- The body is made of a bioresorbable material.
- The anchorage member is patient specific.
- The glenoid implant further comprises a bone fastening screw intended to be screwed into cortical bone of the glenoid, the bone fastening screw being operable to be axially passed through the body so that a threaded rod of the bone fastening screw protrudes axially from the body to be screwed into cortical bone of the glenoid while a threaded head of the bone fastening screw is screwed in a complementary threaded distal hole of the body.

Embodiments of the invention will be better understood from reading the description which will follow, which is given solely by way of example and with reference to the drawings in which:

FIG. 4 is an elevational view along the arrow IV of FIG. 2;

FIG. 5 is an elevational view along the arrow V of FIG. 4;

FIG. 6 is a cross-sectional view along the line VI-VI of FIG. 5;

FIG. 19 is a perspective view of a coupling screw of the set of FIG. 1;

FIG. 20 is a perspective view of another coupling screw of the set of FIG. 1;

Figure 33:
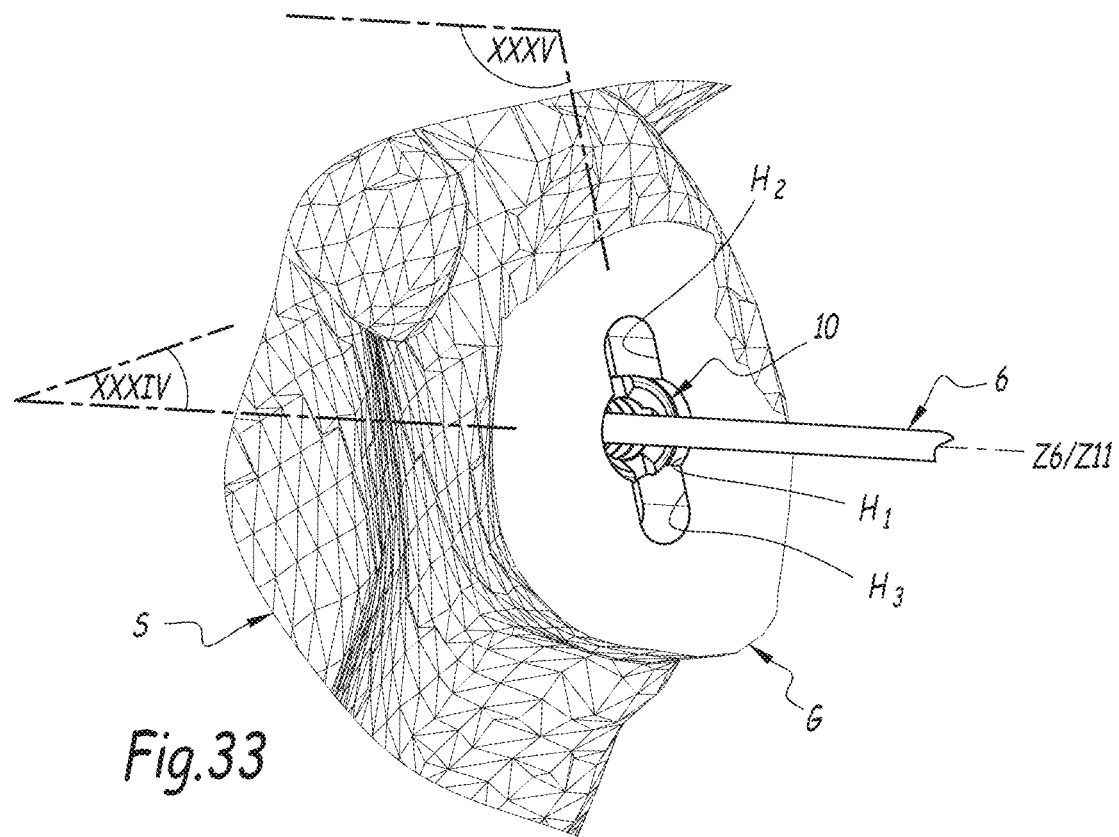
Figure 34:
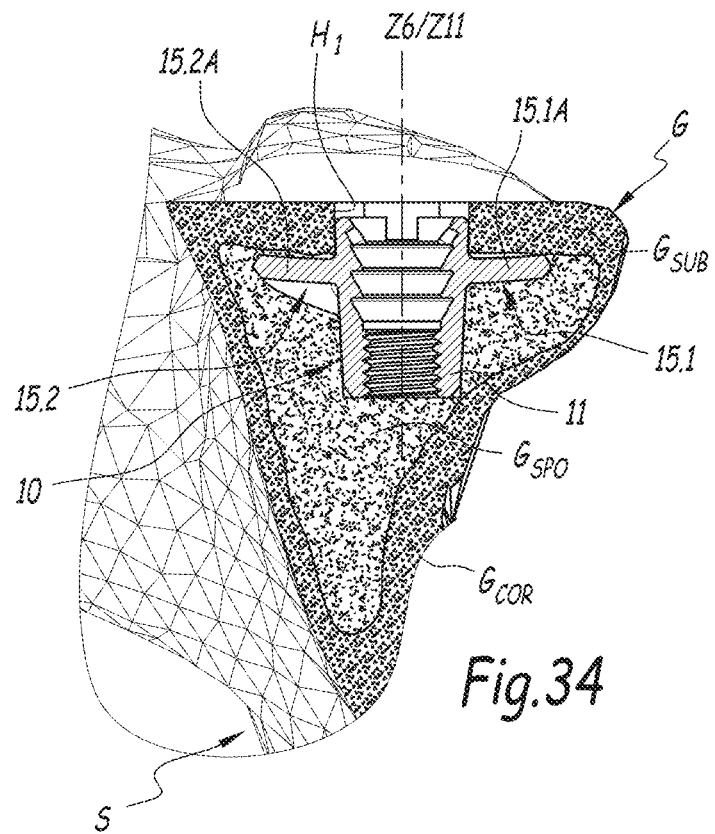
FIGS. 34 and 35 are schematic cross-sectional views respectively in the plane XXXIV and in the plane XXXV of FIG. 33.
Figure 35:
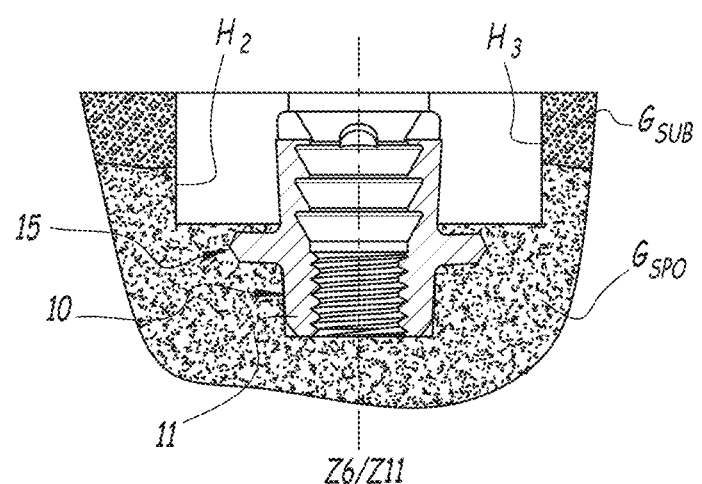
Figure 36:
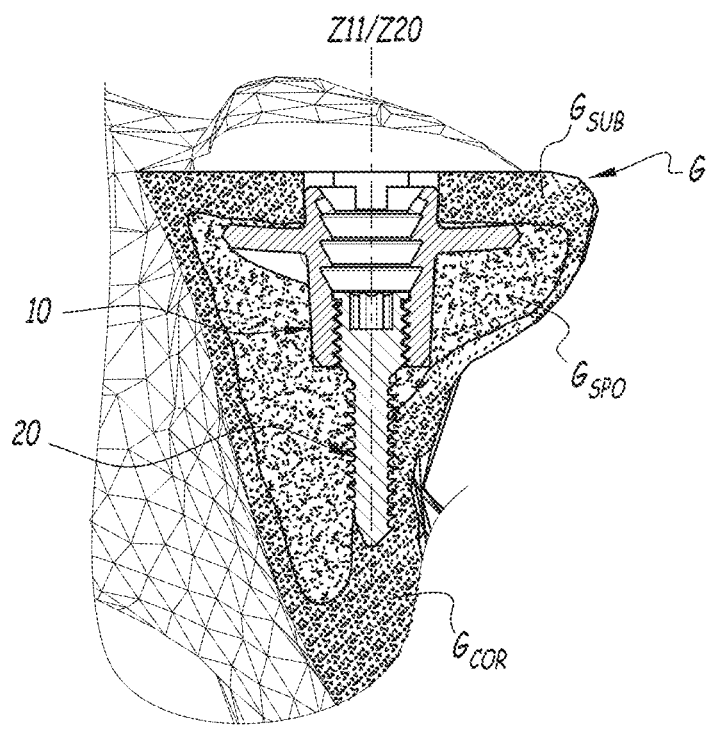
Figure 37:
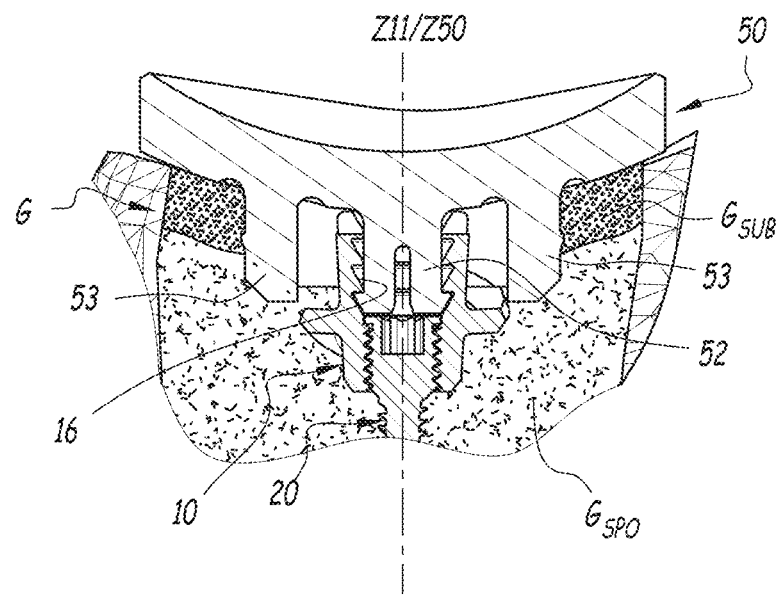

FIGS. 36 and 37 are schematic cross-sectional views showing respectively two successive steps for completing the anchorage member as implanted in FIG. 33 in order to provide an anatomic glenoid implant, the plane of FIG. 36 being similar to the one of FIG. 34 whereas the plane of FIG. 37 is similar to the one of FIG. 35; and FIGS. 38 to 42 are schematic cross-sectional views respectively showing four successive steps for completing the anchorage member as implanted in FIG. 33 in order to provide a reversed glenoid implant, the plane of the FIGS. 38 to 42 being similar to the one of FIG. 35.

Figure 1:
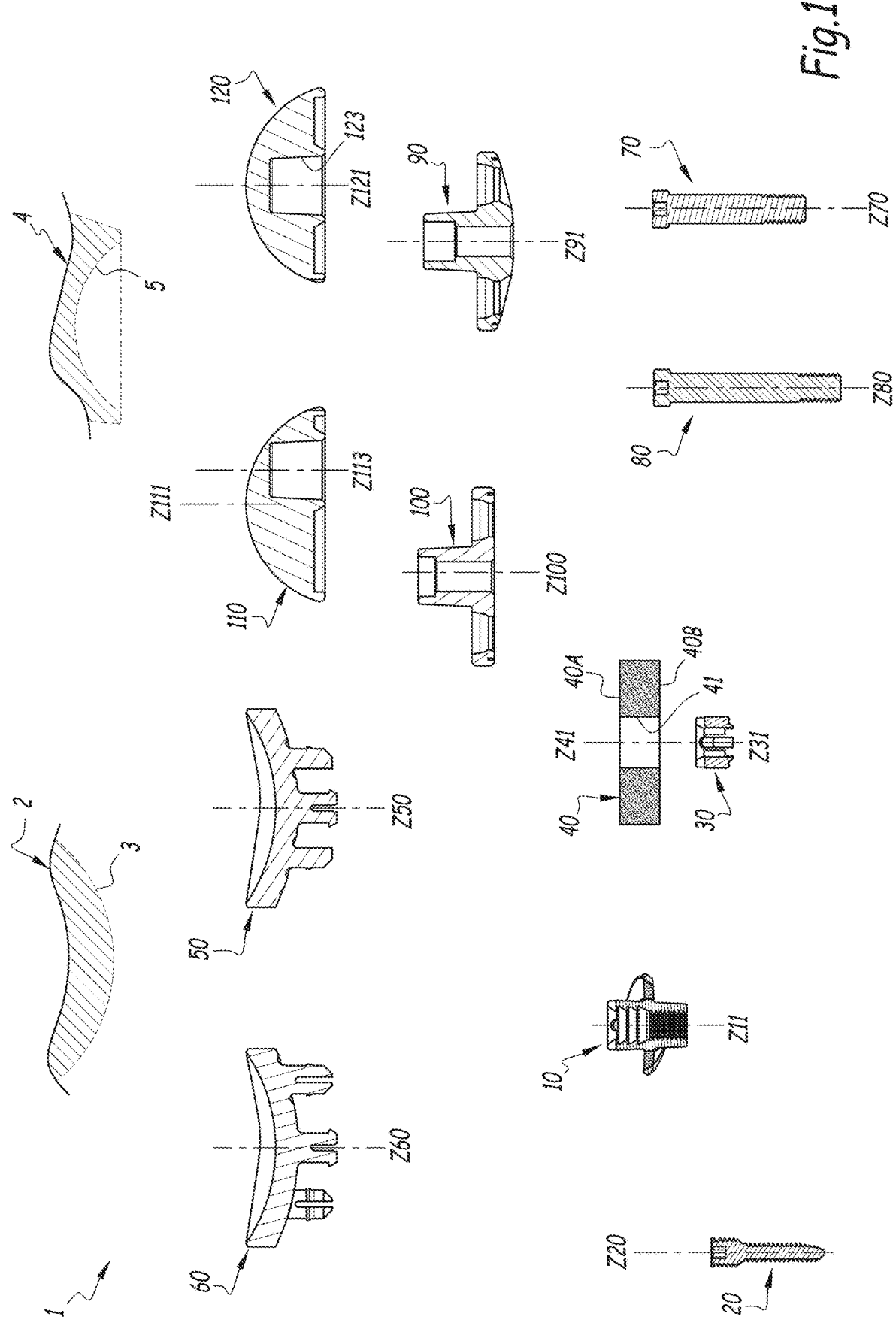
FIG. 1 is a cross-sectional view of a set for a glenoid implant.

FIG. 1 shows a set 1 of prosthetic components from which a glenoid implant can be obtained by assembling at least some of these components. In some embodiments as the one shown in FIG. 1, the set 1 comprises an anchorage member 10, a bone fastening screw 20, a spacer 30, a bone graft 40, a first insert 50, a second insert 60, a first coupling screw 70, a second coupling screw 80, a first baseplate 90, a second baseplate 100, a first glenosphere 110 and a second glenosphere 120. One or the other of the inserts 50 and 60 corresponds to an anatomic articulating member (AAM) for a glenoid implant obtained from the set 1. Each of the combinations of one or the other of the glenospheres 110 and 120, with one or the other of the baseplates 90 and 100 and with one or the other of the coupling screws 70 and 80 corresponds to a reversed articulating member (RAM) for a glenoid implant obtained from the set 1.

In some embodiments, each of the components 10, 20, 30, 40, 50, 60, 70, 80, 90, 100, 110 and 120 or at least one of these components is provided within the set 1 in at least two different sizes which are respectively adapted to different patient morphologies. In some embodiments, each of the components 10, 20, 30, 40, 50, 60, 70, 80, 90, 100, 110 and 120 or at least one of these components is patient-specific in the sense that the component in question includes certain geometric features which are made to closely conform as mirror-images of corresponding geometric features of a patient's anatomy which may be gathered during a preoperative planning stage based on tridimensional computer images of the corresponding anatomy.

Referring now to FIGS. 2 to 6, the anchorage member 10 is shown alone. The anchorage member 10 includes a body 11 which in use, is introduced into the glenoid of a patient. The body 11 defines an axis Z11 on which the body 11 is centered and which is considered as extending in a proximodistal direction. In some embodiments as the one of the FIGS. 2 to 6, the body 11 has a tubular shape that is centered on the axis Z11. The body 11 is thus provided with an inner bore 12 which axially extends from a proximal end 11A of the body 11 to a distal end 11B of the body 11, the inner bore 12 emerging on these proximal and distal ends 11A and 11B.

At its proximal end 11A, the body 11 is provided with a driving feature 13 for removably coupling the body 11 with a complementary tool so as to drive the body into the glenoid during implantation of the anchorage member 10. The driving feature 13 can thus allow driving the body 11 in rotation around the axis Z11. In some embodiments as the one shown in the FIGS. 2 to 6, the driving feature 13 includes indentations 13.1 and 13.2 which are provided on the proximal end 11A of the body 11, especially on a free edge of this proximal end 11A, and which are distributed around the axis Z11.

The body 11 has an outer face 14 extending from the proximal end 11A to the distal end 11B. The outer face 14 can be cylindrical or slightly frustoconical and convergent towards the distal end 11B, while being centered on the axis Z11 in both cases.

On the outer face 14, the body 11 is provided with a thread 15 which is designed to be screwed into the glenoid when the body 11 is driven in rotation around the axis Z11, as explained in detail thereafter. In some embodiments as the one shown in the FIGS. 2 to 6, the thread 15 includes two portions of helix 15.1 and 15.2 which wrap around the outer face 14 of the body 11. The portions of helix 15.1 and 15.2 are symmetrical to each other with respect to the axis Z11. As clearly shown in FIGS. 2 to 4, each portion of helix 15.1, 15.2 wraps around the body 11 over less than one turn and more than half of one turn. Besides, each portion of helix 15.1, 15.2 has a lead between five and twenty-five millimeters, preferably between eight and twenty-two millimeters, preferably between ten and twenty millimeters, and preferably between twelve and eighteen millimeters, the lead being the distance along the axis Z11 that is covered by one turn of the body 11, i.e. by rotating the body 11 over 360°. The portions of helix 15.1, 15.2 are thus designed and dimensioned to entirely pass through a subchondral layer of the glenoid and to have respective proximal ends 15.1A and 15.2A which are engaged with underside of this subchondral bone layer at the end of implantation of the anchorage member 10. Moreover, in some embodiments as the one shown in the FIGS. 2 to 6, each of the portions of helix 15.1, 15.2 has a width, i.e. a dimension radially protruding from the outer face 14 of the body 11, which gradually decreases from its proximal end 15.1A, 15.2A to a distal end 15.1B, 15.2B of the portion of helix, as clearly shown in FIGS. 4 and 5.

Figure 2:
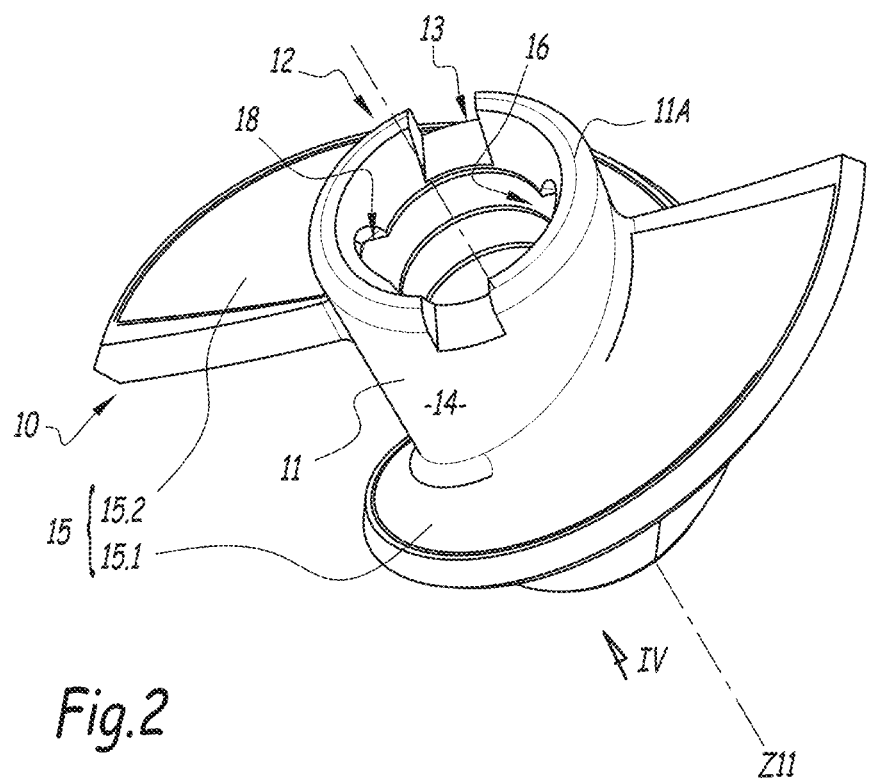
FIG. 2 is a perspective view of an anchorage member of the set of FIG. 1.
Figure 3:
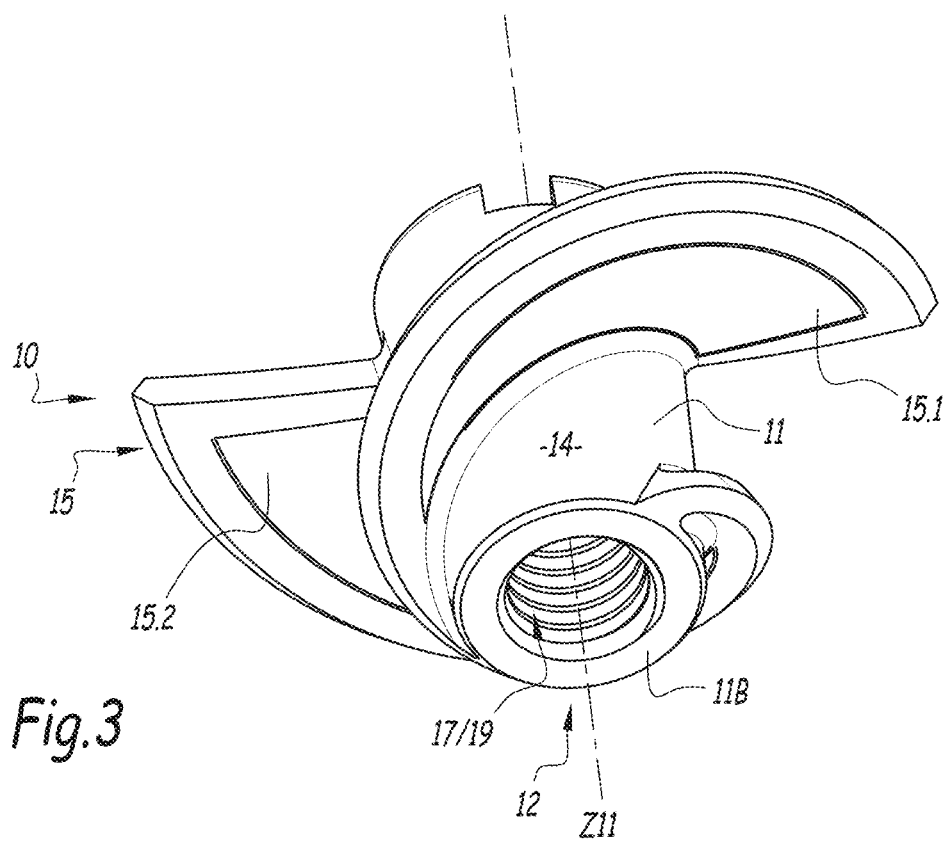
FIG. 3 is a view similar to FIG. 2, having a different angle of observation.

Within its inner bore 12, the body 11 is provided both with a first feature 16, that is observable in FIG. 2, and with a second feature 17 that is observable in FIG. 3, the first feature 16 and the second feature 17 being distinct from each other as clearly shown in FIG. 6. The first feature 16 is designed to cooperate with the aforesaid anatomic articulating member AAM so as to fixedly couple the body 11 with the anatomic articulating member AAM when the anchorage member 10 is assembled with this anatomic articulating member. The second feature 17 is designed to cooperate with the aforesaid reversed articulating member RAM so as to couple the body 11 with this reversed articulating member RAM when the anchorage member 10 is assembled with this reversed articulating member. Thus, the first feature 16 and the second feature 17 do not have the same function. From a structural point of view, they differ from each other in shape.

In some embodiments as the one shown in the FIGS. 2 to 6, in addition to be shaped differently from each other, the first feature 16 and the second feature 17 are located at respective axial levels of the body 11, the axial levels being different from each other: as clearly shown in FIG. 6, the first feature 16 and the second feature 17 are disposed along a length of the axis Z11. In some embodiments as the one shown in the FIGS. 2 to 6, the first feature 16 being axially closer to the proximal end 11A of the body 11 whereas the second feature is axially closer to the distal end 11B of the body 11. In some other embodiments, the respective levels of the first feature 16 and of the second feature 17 are reversed, the first feature being thus axially closer to the distal end 11B of the body 11.

In some embodiments as the one shown in the FIGS. 2 to 6, the first feature 16 comprises, or even consists of, a corrugated hole 16.1, that is centered on the axis Z11 and that forms a proximal part of the inner bore 12, and the second feature 17 comprises, or even consists of, a threaded hole 17.1, that is centered on the axis Z11 and that forms a distal part of the inner bore 12. The technical interest of these two shapes for the features 16 and 17 will appear thereafter.

In some embodiments as the one shown in the FIGS. 2 to 6, the body 11 is also provided with an attaching feature 18 which is designed to cooperate with the spacer 30 so as to removably attach the body 11 and the spacer 30 together when the body is assembled to the spacer. This attaching feature 18 is arranged at a proximal part of the body 11. In some embodiments as the one shown in the figures, the attaching feature 18 is thus located within a proximal part of the inner bore 12, especially axially between the first feature 16 and the edge forming the proximal end 11A of the body 11. In other (not shown) embodiments, the attaching feature is not located within the inner bore 12 but is provided at the edge forming the proximal end 11A of the body 11 and/or at a proximal part of the outer face 14 of the body 11.

In some embodiments as the one shown in the FIGS. 2 to 6, the attaching feature 18 comprises recessed notches 18.1 and 18.2, which are distributed around the axis Z11. As shown by FIG. 6, each of the notches 18.1 and 18.2 has a bottom that is closed in the proximal direction so as to axially retain the spacer 30 in the proximal direction with respect to the body 11 when the anchorage member 10 and the spacer 30 are assembled together. In some (not shown) embodiments, the attaching feature 18 is partly or totally formed by the first feature 16 of the inner bore 12 of the body 11.

In some embodiments as the one shown in FIGS. 2 to 6, the body 11 is also provided with a threaded hole 19 which is designed to cooperate with the bone fastening screw 20 so that this bone fastening screw 20 can be screwed in the threaded hole 19 when the anchorage member 10 and the bone fastening screw 20 are assembled together. The threaded hole 19 is arranged at a distal part of the body 11. The threaded hole opens outside the body in the distal direction whereas the threaded hole 19 opens in the inner bore 12 in the proximal direction. In some embodiments as the one shown in the FIGS. 2 to 6, the threaded hole 19 is partially or totally formed by the second feature 17 of the inner bore 12. In other (not shown) embodiments, the threaded hole 19 is in the distal extension of the inner bore 12, being centered or not on the axis Z11.

In some embodiments, the body 11 is either made of metallic alloy or made of bioresorbable material.

Figure 7:
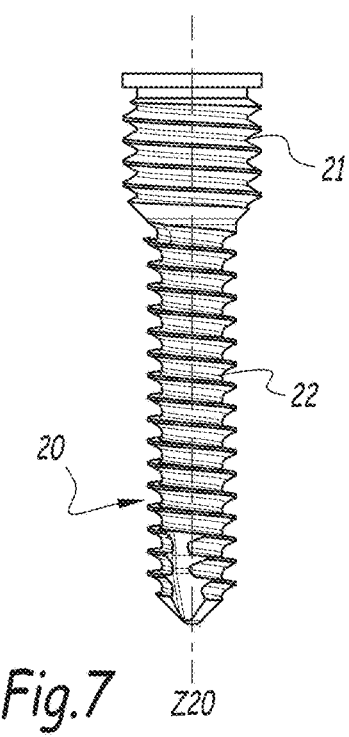
FIG. 7 is a side view of a bone fastening screw of the set of FIG. 1.
Figure 8:
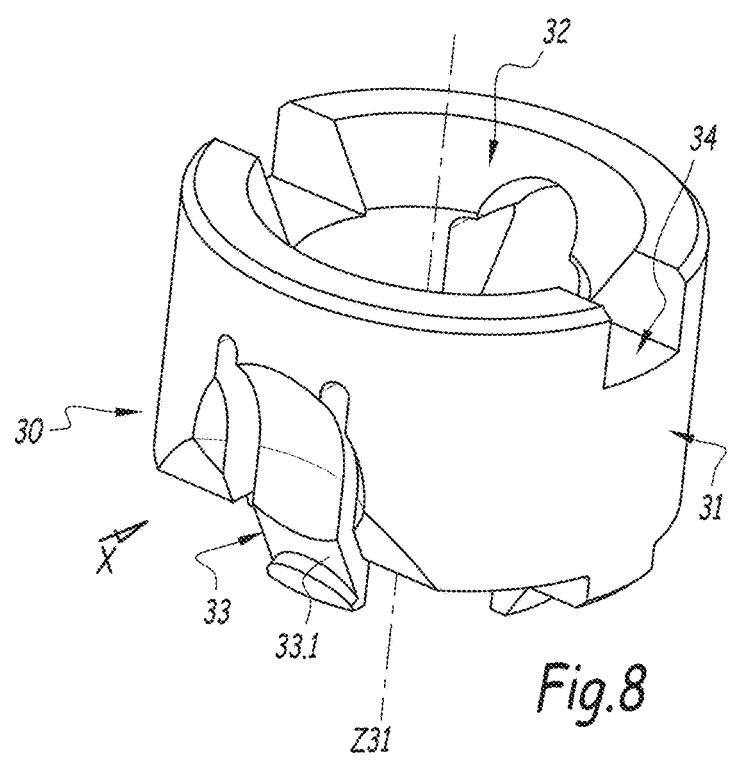
FIG. 8 is a perspective view of a spacer of the set of FIG. 1.
Figure 9:
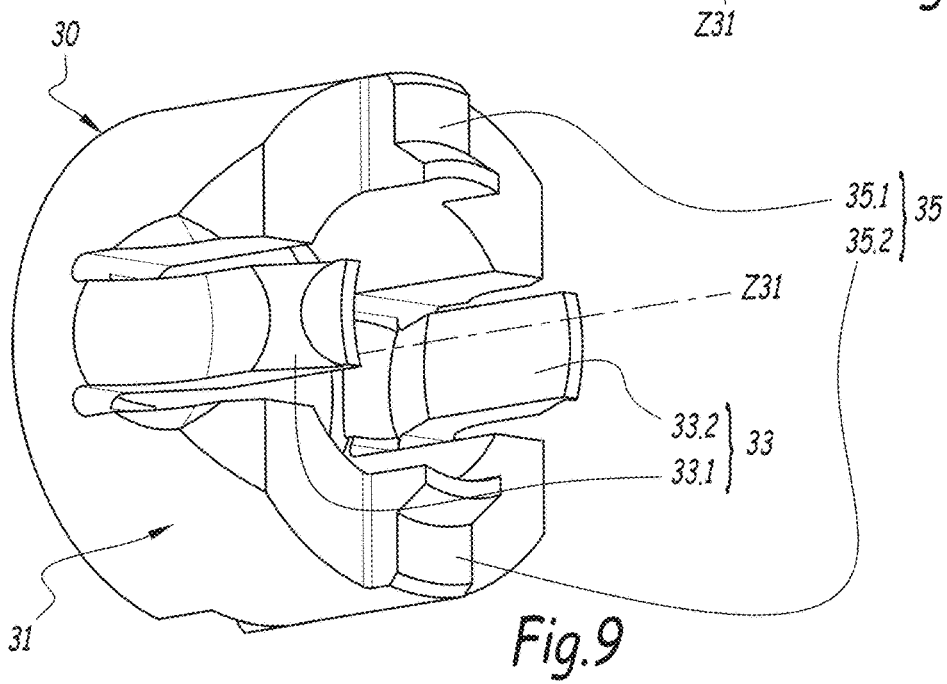
FIG. 9 is a view similar to FIG. 8, having a different angle of observation.
Figure 10:
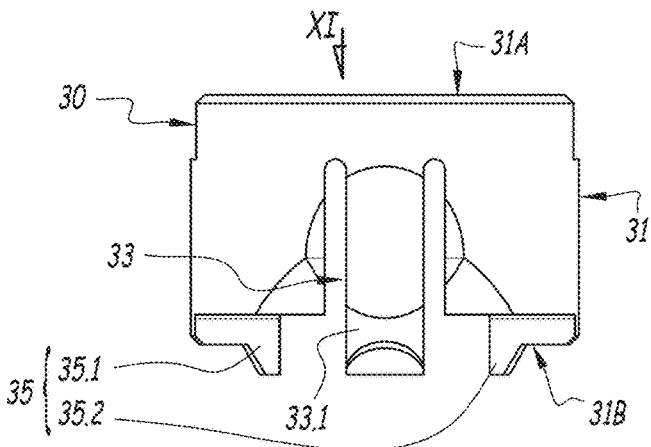
FIG. 10 is an elevational view along the arrow X of FIG. 8.
Figure 11:
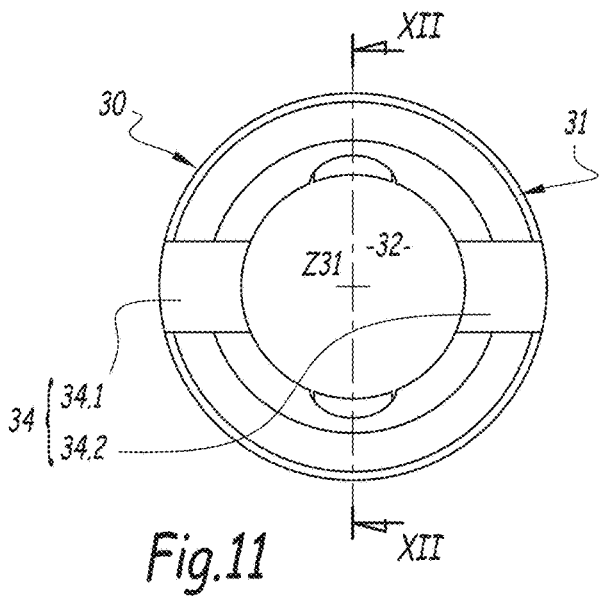
FIG. 11 is an elevational view along the arrow XI of FIG. 10.
Figure 12:
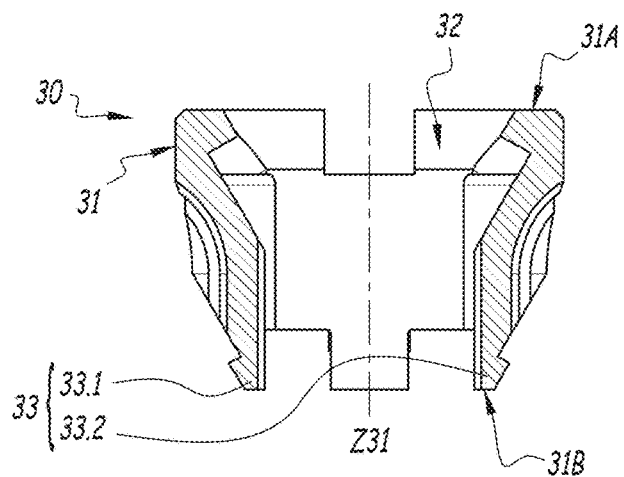
FIG. 12 is a cross-sectional view along the line XII-XII of FIG. 11.

Referring now to FIG. 7, the bone fastening screw 20 is shown alone. This screw defines a longitudinal axis Z20, on which the screw is centered and which extends in the proximodistal direction. The screw 20 includes a head 21 and a rod 22, which are each centered on the axis Z20 and which follow each other in the direction of this axis. The head 21 forms a proximal part of the screw 20 and is threaded complementarily to the threaded hole 19 of the anchorage member 10. The rod 22 forms a distal part of the screw 20 and is also threaded. In some embodiments as the one shown in FIG. 7, the rod 22 has a diameter which is smaller than the diameter of the head 21.

In use, the bone fastening screw 20 can be axially passed through the body 11 of the anchorage member 10 so that the rod 22 protrudes axially from the body while the head 21 is screwed in the threaded hole 19 of the body 11. Thus, when the head 21 is arranged within the threaded hole 19 of the body 11, the rod 22 is arranged outside of this body 11, being located on the distal side of the body 11. In that way, the rod 22 can be screwed into the glenoid of a patient, especially into cortical bone, so that the screw 20 fastens the anchorage member 10 to the glenoid, especially cortical bone thereof.

Referring now to FIGS. 8 to 12, the spacer 30 is shown alone. The spacer 30 comprises a body 31 which defines an axis Z31 extending in the proximodistal direction. The body 31 has a tubular shape centered on the axis Z31. The spacer 30 is thus provided with an inner bore 32, that is centered on the axis Z31 and that extends from a proximal end 31A of the body 31 to a distal end 31B of the body 31.

In use, the spacer 30 is designed to be arranged on the proximal side of the body 11 of the anchorage member 10 so that the inner bores 12 and 32 are in axial extension or alignment one with the other, especially aligning the axis Z11 and Z31. In some embodiments, the body 31 can extend as a coaxial extension of the body 11 in the direction of the axis Z11. In any case, the spacer 30 can, in use, be axially interposed between the body 11 and either the aforesaid anatomic articulating member AAM when the anchorage member 10 and this anatomic articulating member are assembled together, or the aforesaid reversed articulating member RAM when the anchorage member 10 and this reversed articulating member are assembled together.

In some embodiments as the one shown in the FIGS. 8 to 12, the body 31 is provided with an attaching feature 33 which is designed to cooperate with the attaching feature 18 of the body 11 so as to removably attach the bodies 11 and 31 when the anchorage member 10 and the spacer 30 are assembled together. The attaching feature 33 is arranged at a distal end of the body 31. In some embodiments as the one shown in the FIGS. 8 to 12, the attaching feature 33 is provided at the edge forming the distal end 31B of the body 31 and comprises tabs 33.1 and 33.2, which are distributed around the axis Z31 and which are flexibly connected to the rest of the body 31: in use, when the anchorage member 10 and the spacer 30 are assembled together, the tabs 33.1 and 33.2 are respectively received in the recessed notches 18.1 and 18.2, their introduction requiring them to deform elastically towards the axis Z31 whereas once they are completely introduced in the recessed notches 18.1 and 18.2, the free end of each of the tabs 33.1 and 33.2 are resiliently biased into the bottom of the corresponding notch so as to axially retain the body 31 with respect to the body 11. In other words, the tabs 33.1 and 33.2 can be clipped onto the recessed notches 18.1 and 18.2. Of course, the tabs 33.1 and 33.2 and the recessed notches 18.1 and 18.2 are only an example for the attaching features 18 and 33, which allows a distal part of the body 31 to be clipped on a proximal part of the body 11. More generally, the arrangement of the attaching feature 33 on the body 31 and the shape of this attaching feature 33 are adapted to the arrangement of the attaching feature 18 on the body 11 and the shape of this attaching feature 18 so as to allow the spacer 30 to be added and attached to the anchorage member 10.

In some embodiments as the one shown in the FIGS. 8 to 12, the body 31 is provided with a driving feature 34 for removably coupling the body 31 with a complementary tool so as to drive the body 31 during implantation of the spacer 30. In practice, this driving feature 34 of the spacer 30 can be functionally or even structurally similar to the driving feature 13 of the body 11 of the anchorage member 10. In particular, similarly to what has been described above for the driving feature 13, the driving feature 34 can include indentations 34.1 and 34.2 provided on the edge forming the proximal end 31A of the body 31. Besides, whatever the type of the driving feature 34 of the spacer 30, the body 31 can be designed to transmit drive movements to the anchorage member 10 when the latter is assembled with the spacer 30 during implantation of them. Such a drive transmission can be at least partly provided by the cooperation between the attaching feature 18 of the body 11 and the attaching feature 33 of the body 31. In some embodiments as the one shown in the FIGS. 8 to 12, such a drive transmission can also be at least provided by a dedicated transmitting feature 35 which is designed to cooperate with the driving feature 13 of the body 11 so as to transmit drive movements from the spacer 30 to the anchorage member 10, especially to transmit rotational drive movements around the axes Z31 and Z11, when the anchorage member 10 and the spacer 30 are assembled together. Of course, the arrangement of the transmitting feature 35 on the body 31 and the shape of this transmitting feature 35 are adapted to the arrangement of the driving feature 13 on the body 11 and the shape of this driving feature 13: in the example of the FIGS. 8 to 12, the transmitting feature 35 comprises projections 35.1 and 35.2, which are provided on the edge forming the distal end 31B of the body 31 and which are respectively received in the indentations 13.1 and 13.2 so as to connect in rotation the bodies 11 and 31 together.

Referring back to FIG. 1, the bone graft 40 will be now described. The bone graft 40 is annular shaped and is conformed to surround the body 31 of the spacer 30. To this end, the bone graft 40 is provided with a through hole 41, which is centered on an axis Z41 extending in the proximodistal direction and which is complementary to the body 31. The through hole 41 axially extends from a proximal end face 40A of the bone graft 40 to a distal end face 40B of the bone graft, these end faces 40A and 40B being separated by the axial dimension of the bone graft 40, which substantially corresponds to the axial dimension of the spacer 30.

In use, the body 31 is received within the through hole 41, aligning the axis Z31 with the axis Z41 so that the bone graft 40 extends all over the spacer 30 around its axis Z41 and can be arranged axially between the glenoid of the patients and either the aforesaid anatomic articulating member AAM or the aforesaid reversed articulating member RAM, as explained in detail thereafter. In other words, the spacer 30 may be at least partially or entirely retained within the bone graft 40.

In some embodiments, the bone graft 40 is an autologous graft, an allograft or a synthetic graft.

Figure 13:
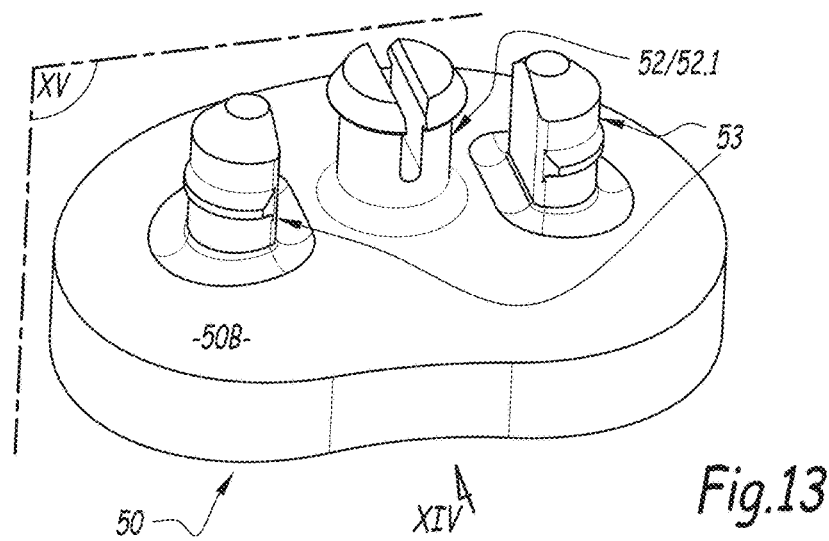
FIG. 13 is a perspective view of an insert of the set of FIG. 1.
Figure 14:
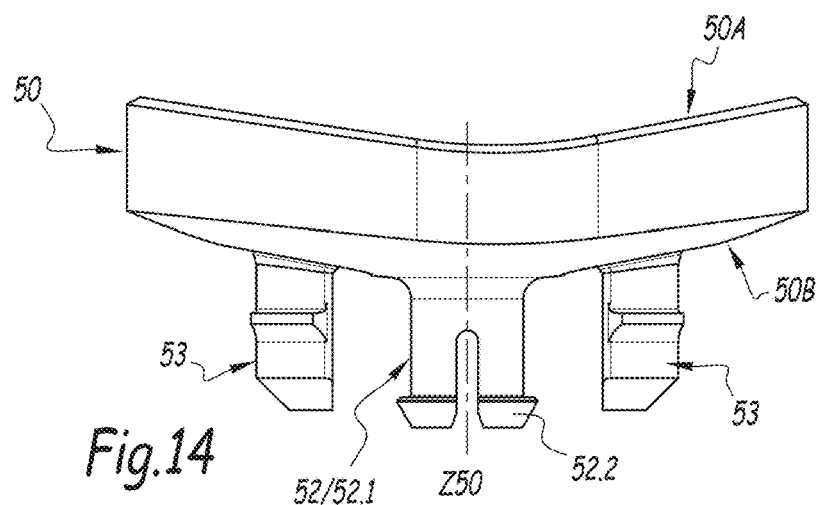
FIG. 14 is an elevational view along the arrow XIV of FIG. 13.
Figure 15:
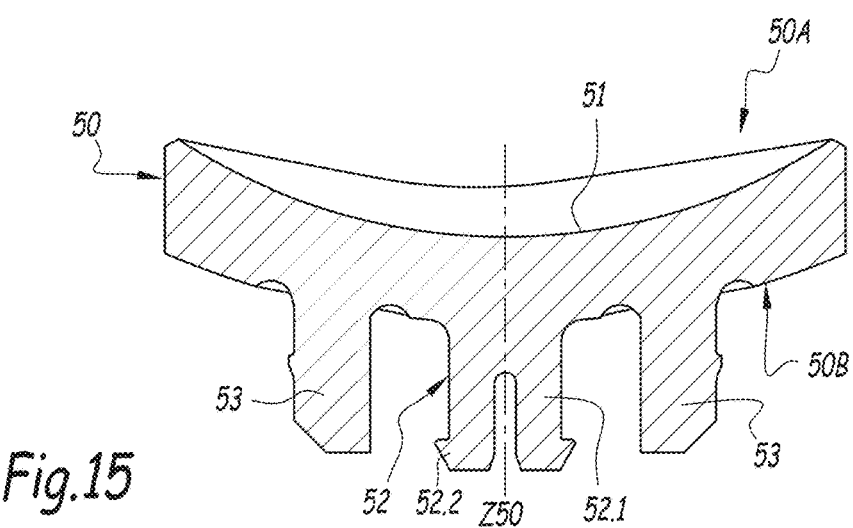
FIG. 15 is a cross-sectional view in the plane XV of FIG. 13.

Referring now to FIGS. 13 to 15, the first insert 50 is shown alone. The insert 50 defines a central axis Z50 that extends in the proximodistal direction. The insert 50 has a proximal face 50A on which is formed a concave articulating surface 51. In use, this concave articulating surface 51 is provided to articulate with a complementary convex articulating surface 3 of a humeral implant 2 that is only partially drawn in FIG. 1, in dotted lines. The type of this humeral implant 2 is not limitative as long as the articulating surface 3 thereof is convex and complementary to the concave articulating surface 51 of the insert 50.

Furthermore, the insert 50 has a distal face 50B which is provided with an anatomic coupling feature 52. This coupling feature 52 is designed to cooperate with the first feature 17 of the anchorage member so as to fixedly couple the anchorage member 10 with the insert 50 and therefore with the aforesaid anatomic articulating member AAM when this latter corresponds to the first insert 50.

In some embodiments as the one shown in the FIGS. 13 to 15, the coupling feature 52 of the insert 50 at least partly protrudes from the distal face 50B so as to be coaxially received within the inner bore 12 of the anchorage member 10 and to cooperate with the first feature 16 by fitting along the axis Z11 when the anchorage member 10 and the insert 50 are assembled together. In that case and as shown by the FIGS. 13 to 15, the coupling feature 52 can comprise a central peg 52.1, which is centered on the axis Z50 and which is designed to be fitted with the first feature 16 within the inner bore 12 by snap fit: in particular, the central peg 52.1 is shaped to be axially received and to be wedged in the corrugated hole 16.1 of the first feature 16 when the anchorage member 10 and the insert 50 are assembled together. At its proximal end, this central peg 52.1 can be integral with the rest of the insert 50 whereas the rest of the central peg 52.1 can be either smooth or provided with at least one peripheral rib 52.2 designed to interfere with at least one of the corrugations of the corrugated hole 16.1. Moreover, the central peg 52.1 can be slotted, as in the example shown in the FIGS. 13 to 15, in order to facilitate the introduction of the central peg 52.1 within the inner bore 12 and to improve the axial fitting of this central peg with the first feature 16. More generally, the coupling feature 52 can have various types, being adapted to the type of the first feature 16, preferably so that the coupling feature 52 and the first feature 16 cooperate with each other by fitting along the aligned axes Z11 and Z50.

The distal face 50B of the insert 50 is also provided with two lateral pegs 53 which at least partly protrude from this distal face 50B. These lateral pegs 53 are distributed around the axis X50 and are designed to interfere with the glenoid of the patient so as to block the insert 50 in rotation around the axis Z50 with respect to the glenoid.

In some embodiments as the one shown in the FIGS. 13 to 15, the lateral pegs are arranged either side of the central peg 52.1, the central peg 52.1 and the lateral pegs 53 being aligned in direction perpendicular to the axis Z50. Besides, each lateral peg 53 is arranged to surround and cover an angular portion of the outer thread 15 of the body 11 when the anchorage member 10 and the insert 50 are assembled together. In particular, the radial distance between the central peg 52.1 and each of the lateral pegs 53 is substantially equal to the sum of wall thickness of the body 11 and of the maximal width of the thread 15, and the face of each of the lateral pegs 53, which radially faces the central peg 52.1, is complementary to the outer contour of the thread 15: in that way, two diametrical opposed portions of the wall of the body 11 are radially sandwiched respectively between the central peg 52.1 and one of the lateral pegs 53 and between the central peg 52.1 and the other lateral peg 53 when the anchorage member 10 and the insert 50 are assembled together. This arrangement can strengthen the cooperation between the coupling feature 52 and the first feature 16 by pinching effect of the body 11 by the lateral pegs 53. At least one further technical interest will be given thereafter.

In some embodiments, the distal face 50B of the insert 50 is at least partly provided with a coating permitting or promoting bone regrowth.

Figure 16:
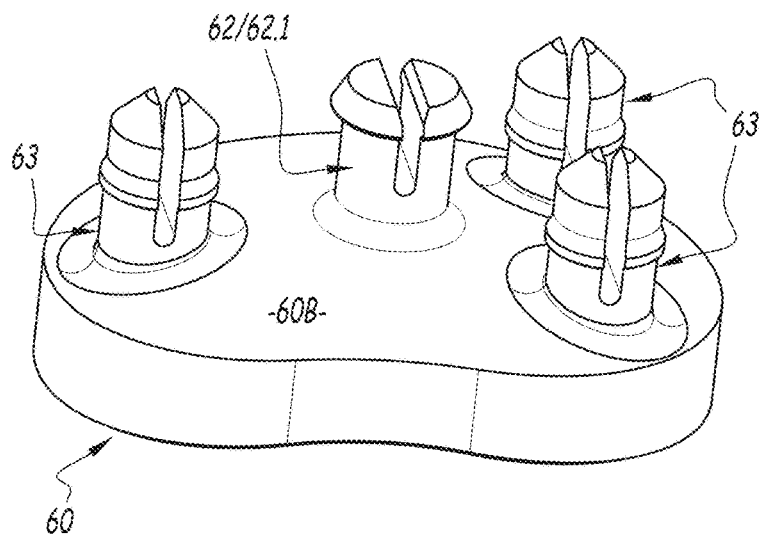
FIGS. 16 to 18 are views which are respectively similar to the FIGS. 13 to 15 and which illustrate another insert of the set of FIG. 1.
Figure 17:
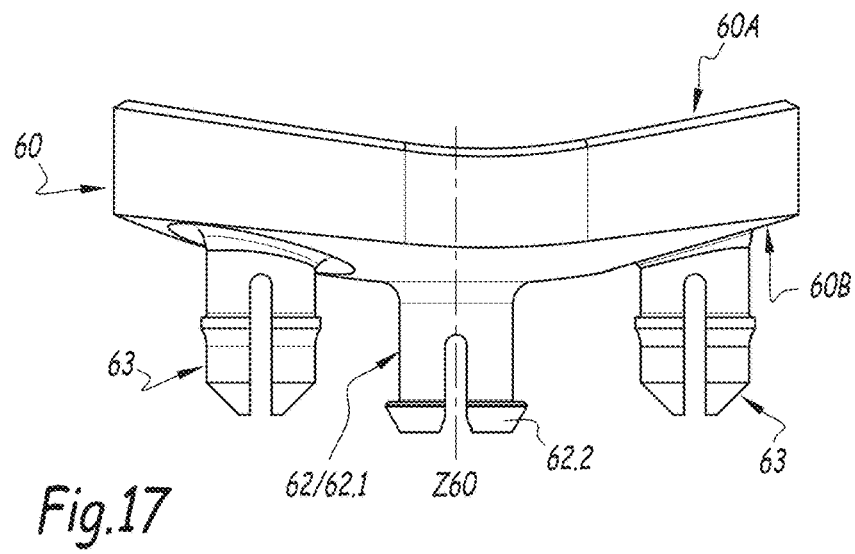
Figure 18:
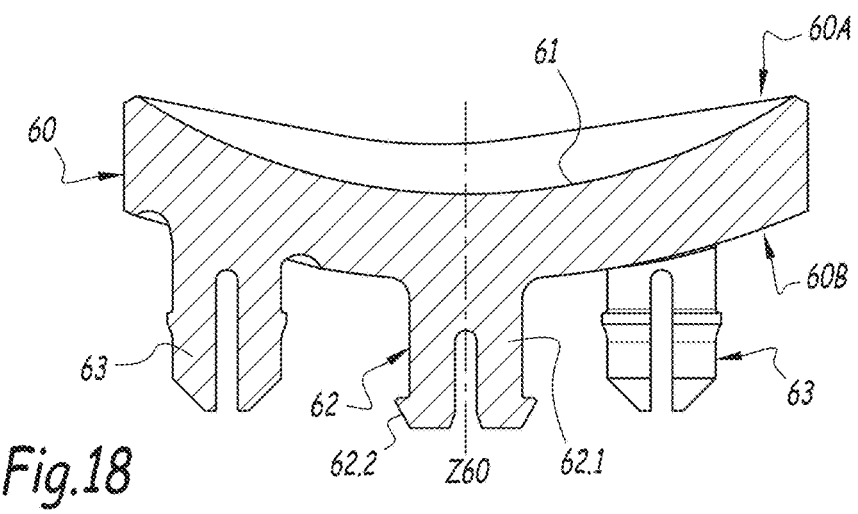

Referring now to the FIGS. 16 to 18, the second insert 60 is shown alone. As is apparent by comparison between the FIGS. 13 to 15 and the FIGS. 16 to 18, the insert 60 has a central axis Z60, a proximal face 60A, a concave articulating surface 61, a distal face 60B, a coupling feature 62, a central peg 62.1 and at least one peripheral rib 62.2, which are respectively similar to the elements Z50, 50A, 51, 50B, 52, 52.1 and 52.2 of the insert 50. The insert 60 differs from the insert 50 by lateral pegs 63. Contrary to the lateral pegs 53 of the insert 50, the lateral pegs 63 are in triplicate, being distributed around the axis Z60, and are spaced from the central peg 62.1 by a radial distance which is greater than the sum of the wall thickness of the body 11 and of the maximal width of the thread 15. In use, the lateral pegs 53 do not interfere with the thread 15 when the anchorage member 10 and the insert 60 are assembled together, but they can still block the insert 60 in rotation around the axis Z60 with respect to the glenoid, by interfering directly with the glenoid.

Referring now to FIG. 19, the first coupling screw 70 is shown alone. This coupling screw 70 defines and is centered on an axis Z70 which extends in the proximodistal direction. The coupling screw 70 includes a proximal head 71 and a distal rod 72. The rod 72 is designed to be axially introduced into the inner bore 12 of the body 11, aligning the axes Z70 and Z11, and to cooperate with the second feature 17 so as to fixedly couple the anchorage member 10 with the aforesaid reversed articulating member RAM by a screw connection when this reversed articulating member and the anchorage member are assembled together. In some embodiments as the one shown here, this screw connection is centered on the axis Z11.

In some embodiments as the one shown in FIG. 19, the rod 72 is provided with a threaded part 72.1 which can be screwed into the threaded hole 17.1 of the second feature 17, by rotating the coupling screw 70 around its axis Z70 within the inner bore 12. In some embodiments as the one shown in FIG. 19, the head 71 is wider than the rod 72, in the sense that the diameter of the head 71 is greater than the diameter of the rod 72.

Referring now to FIG. 20, the second coupling screw 80 is shown alone. This coupling screw is similar to the first coupling screw 70 in that the coupling screw 80 has an axis Z80, a head 81, a rod 82 and a threaded part 82.1 which are respectively similar to the elements Z70, 71, 72 and 72.1 of the coupling screw 70. The coupling screw 80 differs from the coupling screw 70 by its length, i.e. its axial dimension: the rod 82 is axially longer than the rod 72, as clearly shown by comparing the FIGS. 19 and 20. The first coupling screw 70 is used in the aforesaid reversed articulating member RAM when the latter is assembled with the anchorage member 10 without that this anchorage member 10 is assembled with the spacer 30. The second coupling screw 80 is used in the aforesaid reversed articulating member RAM when this latter is assembled with the anchorage member 10 with which the spacer 30 is assembled: in that case, as the spacer 30 is axially interposed between the body 11 and the reversed articulating member, an axial part of the rod 82 is necessarily arranged within the inner bore 32 of the spacer 30 so as to allow the distal part of the rod 82, especially its threaded part 82.1, to cooperate with the second feature 17, after having freely passed in the distal direction through the spacer 30 via the inner bore 32 thereof.

Figure 21:
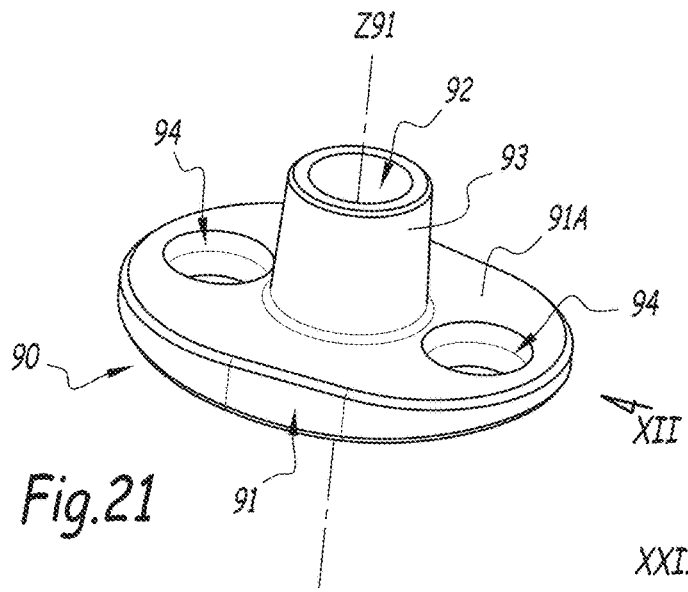
FIG. 21 is a perspective view of a baseplate of the set of FIG. 1.
Figure 22:
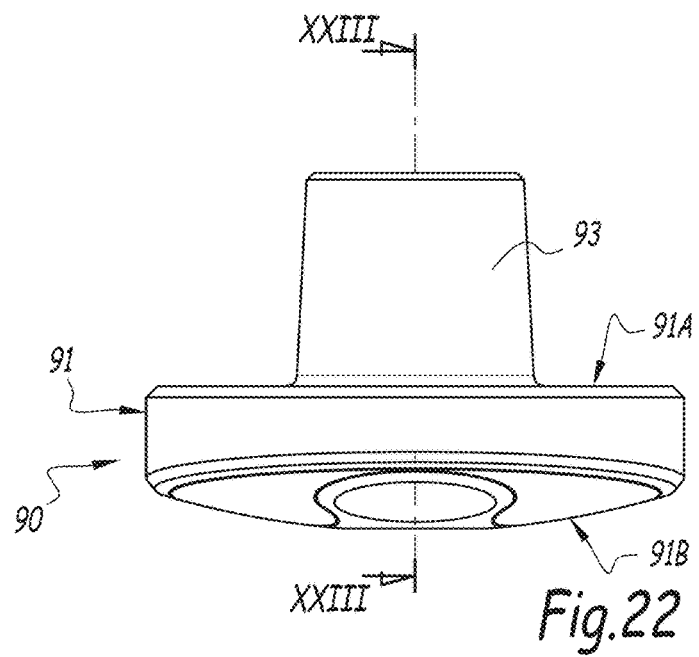
FIG. 22 is an elevational view along the arrow XXII of FIG. 21.
Figure 23:
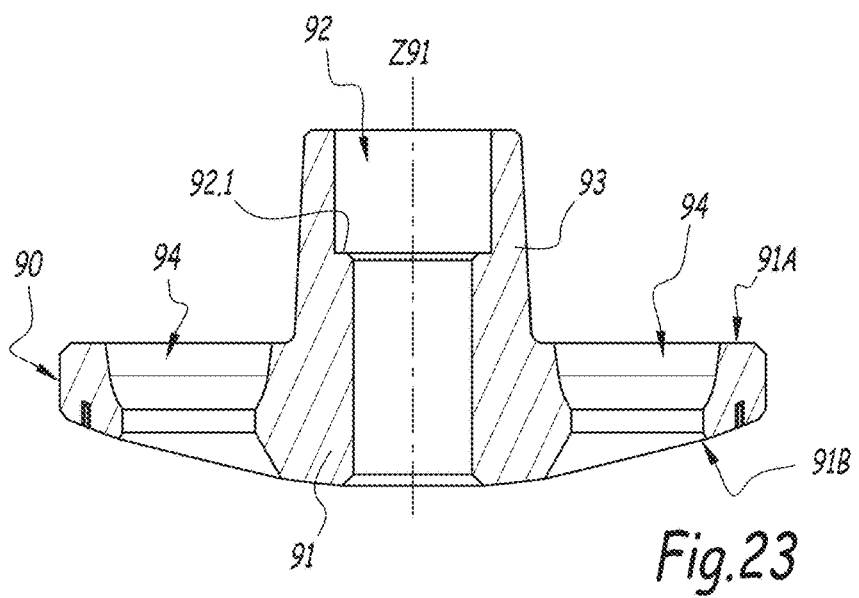
FIG. 23 is a cross-sectional view along the line XXIII-XXIII of FIG. 22.

Turning now to the FIGS. 21 to 23, the first baseplate 90 is shown alone. The baseplate 90 comprises a body 91 defining a central axis Z91 which extends in a proximodistal direction. The body 91 has a proximal face 91A and a distal face 91B. The body 91 is also provided with a central bore 92, which is centered on the axis Z91 and which extends from the proximal face 91A to the distal face 91B. The central bore 92 is designed to coaxially receive indifferently the first coupling screw 70 and the second coupling screw 80 depending on whether the first coupling screw 70 or the second coupling screw 80 is used in the aforesaid reversed articulating member RAM. The rod 72, 82 of this coupling screw 70, 80 can be freely received in the central bore 92 whereas the head 71, 81 can be axially engaged within the central bore so as to axially retain the head in the distal direction while a distal part of the rod 72, 82 protrudes from the distal face 91B of the body 91. In some embodiments as the one shown in the FIGS. 21 to 23, the central bore is provided with an axial bearing surface 92.1 against which the head 71, 81 can be supported in the distal direction.

In some embodiments as the one shown in the FIGS. 21 to 23, the proximal face 91A of the body 91 is provided with a male part 93 of a taper connection intended to be used to fixedly mounted indifferently one and the other of the glenospheres 110 and 120 on the baseplate 90. The male part 93 of this taper connection can be centered on the axis Z91, a part of the central bore 92 being thus delimited by the male part 93 of the taper connection, as clearly shown by FIG. 23.

In some embodiments as the one shown in the FIGS. 21 to 23, the body 91 is also provided with lateral through holes 94 which each extends from the proximal face 91A to the distal face 91B of the body 91. Each of these lateral through holes 94 is designed to receive and engage in the distal direction a bone securing screw, as explained in detail thereafter.

Figure 24:
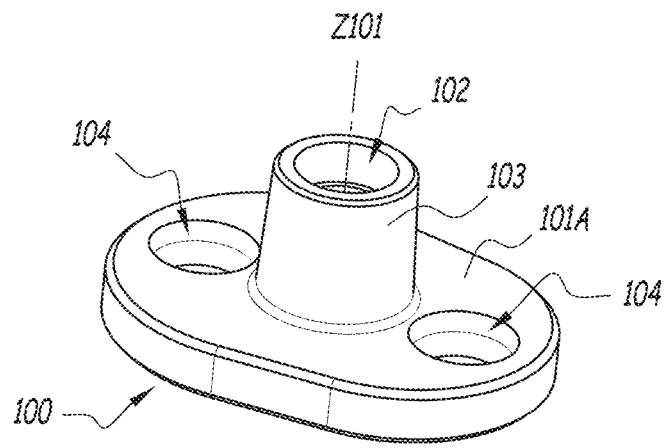
FIGS. 24 to 26 are views which are respectively similar to FIGS. 21 to 23 and which show another baseplate of the set of FIG. 1.
Figure 25:
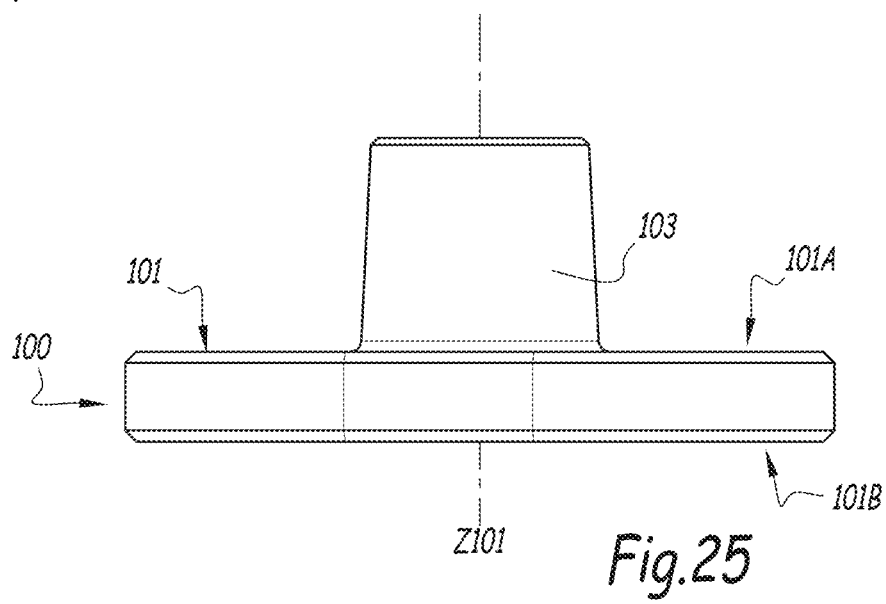
Figure 26:
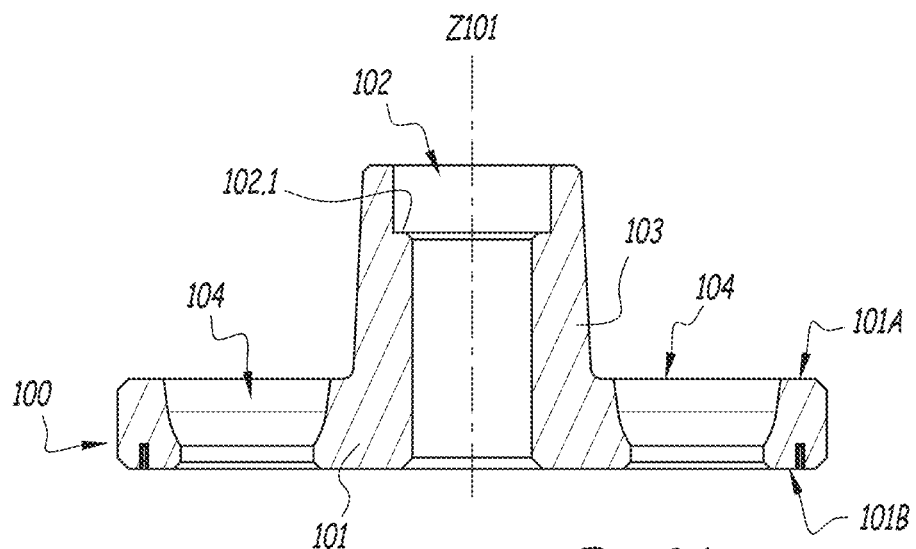
Figure 27:
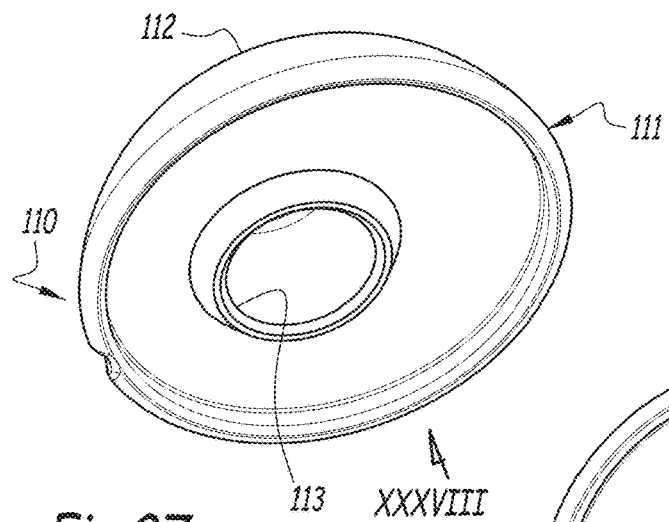
FIG. 27 is a perspective view of a glenosphere of the set of FIG. 1.

Referring now to the FIGS. 24 to 26, the second baseplate 100 is shown alone. As is apparent by comparing the FIGS. 21 to 23 with the FIGS. 24 to 26, the second baseplate 100 has a body 101, a central axis Z101, a proximal face 101A, a distal face 101B, a central bore 102, an axial bearing surface 102.1, a male part 103 of a taper connection, and lateral through holes 104, which are respectively similar to the elements 91, Z91, 91A, 91B, 92, 92.1, 93 and 94 of the first baseplate 90. The second baseplate 100 differs from the first baseplate 90 by its distal face 101B: as clearly shown by the FIGS. 22 and 23, the distal face 91B of the first baseplate is convex whereas the distal face 101B of the second baseplate 100 is substantially planar, being perpendicular to the axis Z101. In use, the distal face 91B, 101B of the baseplates 90 and 100 is intended to be in direct contact with bone tissue, more precisely either the glenoid of a patient or the bone graft 40 axially arranged between the glenoid and indifferently one and the other of the baseplate 90 and 100: therefore, using one or the other of the baseplate 90 and 100 depends on the shape of bone tissue that is to cover by the distal face 91B, 101B of the baseplate, as discussed thereafter.

In some embodiments, the distal face 91B of the baseplate 90 and/or the distal face 101B of the baseplate 100 are at least partly provided with a coating permitting or promoting bone regrowth Referring now to the FIGS. 27 to 30, the first glenosphere 110 is shown alone. The glenosphere 110 comprises a body 111 which corresponds to a portion of a sphere. This body 111 defines a central axis Z111 which extends in the proximodistal direction and on which is centered the aforesaid sphere portion. The body 111 has a proximal face 111A on which is formed a convex articulating surface 112 that is substantially spherical. In use, the convex articulating surface 112 articulates with a concave complementary surface 5 of a humeral implant 4 that is only partially drawn in FIG. 1, in dotted lines. The type of this humeral implant 4 is not limitative as long as the articulating surface 5 thereof is convex and complementary to the concave articulating surface 51 of the insert 50.

The body 111 further has a distal face 111B which is designed to be fixedly mounted indifferently on one and the other of the first and second baseplates 90 and 100, especially by the aforesaid taper connection. In some embodiments as the one shown in the FIGS. 27 to 30, the distal face 111B of the body 11 is provided with a female part 113 of this taper connection and is therefore designed to receive and attach to the male part 93, 103 of the corresponding baseplate 90, 100. The female part 113 of the taper connection is centered on a connection axis Z113 which is aligned with the axis Z91, Z100 of the corresponding baseplate 90, 100 when the corresponding male part 93, 103 of the taper connection cooperates with the female part 113.

Figure 28:
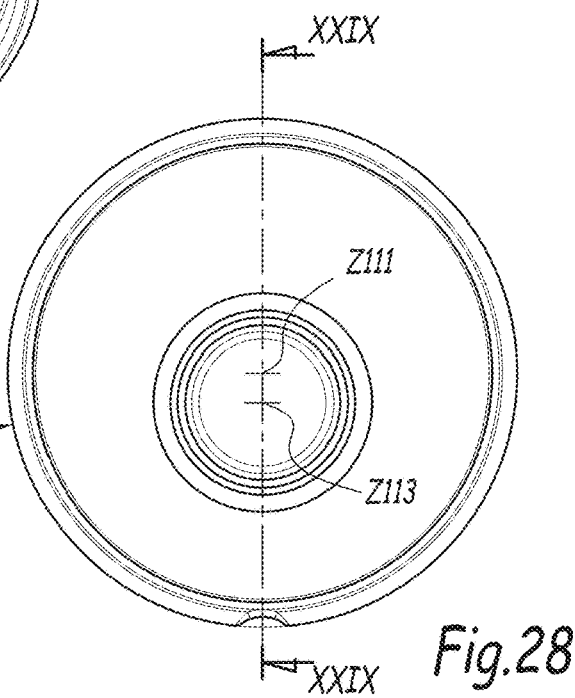
FIG. 28 is an elevational view along the arrow XXVIII of FIG. 27.
Figure 29:
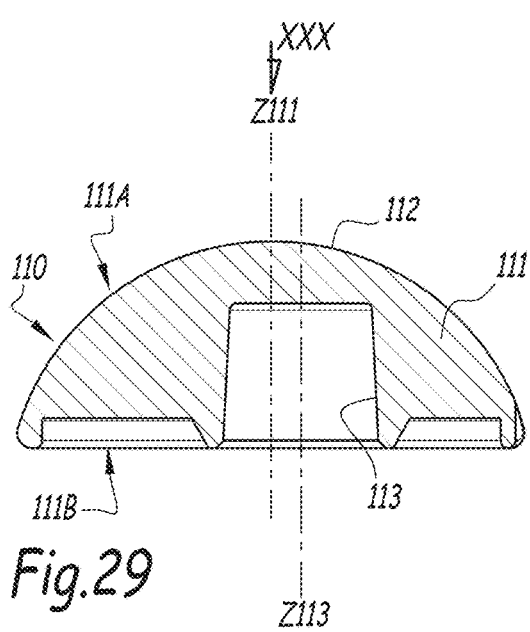
FIG. 29 is a cross-sectional view along the line XXIX-XXIX of FIG. 28.
Figure 30:
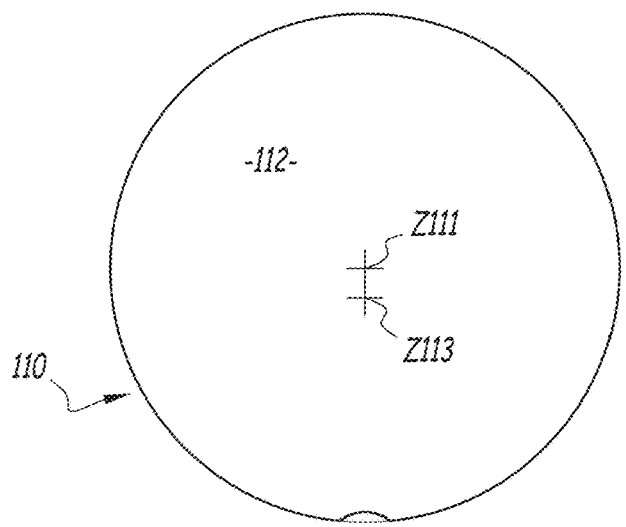
FIG. 30 is an elevational view along the arrow XXX of FIG. 29.

As shown by the FIGS. 28 to 30, the central axis Z111 of the body 111 is both parallel to the connection axis Z113 and offset from this connection axis Z113: when the glenosphere 110 is assembled with indifferently one and the other of the first and second baseplates 90 and 100, the convex articulating surface 112 is eccentric with respect to the corresponding central axis Z91, Z101 of the corresponding baseplate. Thus, the first glenosphere 110 can be considered as being an eccentric glenosphere for a corresponding glenoid implant obtained from the set 1.

Referring back to FIG. 1, the second glenosphere 120 will now be described. This second glenosphere 120 is similar to the first glenosphere 110, except that this second glenosphere 120 is not eccentric. In other words, as shown in FIG. 1, a female part 123 of the aforesaid connection, which is similar to the female part 113 of the first glenosphere 110, is centered on a central axis Z121 of the glenosphere 120, which is similar to the central axis Z111 for the first glenoid 110.

Based on the foregoing, it will be understood that within the aforesaid reversed articulating member RAM, the first coupling screw 70 and the second coupling screw 80 correspond indifferently to a coupling feature that is designed to cooperate with the second feature 17 of the anchorage member so as to couple the reversed articulating member RAM with the anchorage member 10. This coupling feature of the reversed articulating member RAM, which can be designated as a reversed coupling feature, is shaped differently from the anatomic coupling feature 52, 62 of the aforesaid anatomic articulating member AAM. Besides, thanks to its first feature 16 and its second feature 17, the body 11 of the anchorage member 10 is operable to be coupled indifferently with one or with the other of the aforesaid anatomic and reversed articulating members.

The technical aspect, that has just been mentioned, and other technical aspects will now be illustrated in reference to the FIGS. 31 to 42 by examples of using the set 1 in order to obtain two glenoid implants, i.e. an anatomic glenoid implant and a reversed glenoid implant.

Figure 31:
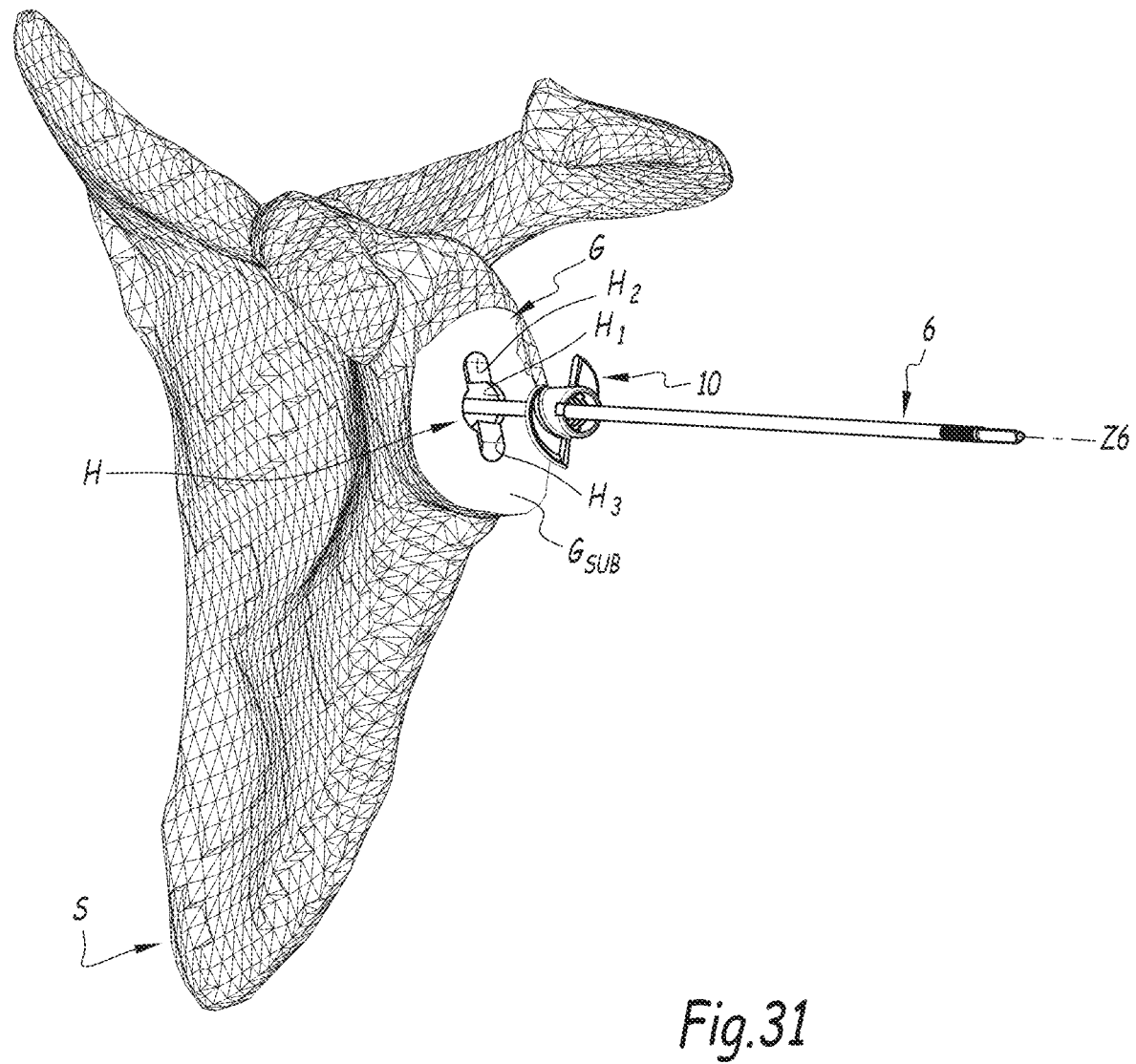
FIGS. 31 to 33 are perspective views which respectively show three successive steps for implanting the anchorage member of FIG. 2 into a glenoid of a human scapula.

FIG. 31 shows a human scapula S having a glenoid G. Before using the set 1, the glenoid G is prepared. Thus, a pin 6 is introduced into the glenoid so as to extend lengthwise in an implantation axis Z6 that is determined by the surgeon. This implantation axis Z6 will form, when using the set 1, the proximodistal direction that has been considered above to describe the set 1. In addition to place the pin 6, the surgeon prepares the glenoid G also by drilling a hole H through the subchondral bone layer $G_{SUB}$ of the glenoid G: as shown in FIG. 31, the hole H is prepared so as to include both a circular central part $H_1$, that is centered on the implantation axis Z6, and to longitudinal slots $H_2$ and $H_3$. The central part $H_1$ is dimensioned to be complementary to the outer face 14 of the body 11 of the anchorage member 10. Each of these slots $H_2$ and $H_3$ extends lengthwise radially to the implantation axis and from the central part $H_1$, these slots $H_2$ and $H_3$ being diametrically opposed to each other with respect to the implantation axis Z6. In practice, the longitudinal direction of the slots $H_2$ and $H_3$ can be substantially vertical with respect to the glenoid, as shown in FIG. 31. On its proximal side, the hole H emerges outside the glenoid G whereas on its distal side, the hole H opens on spongious bone $G_{SPO}$ (FIGS. 34 and 35) of the glenoid G.

Figure 32:
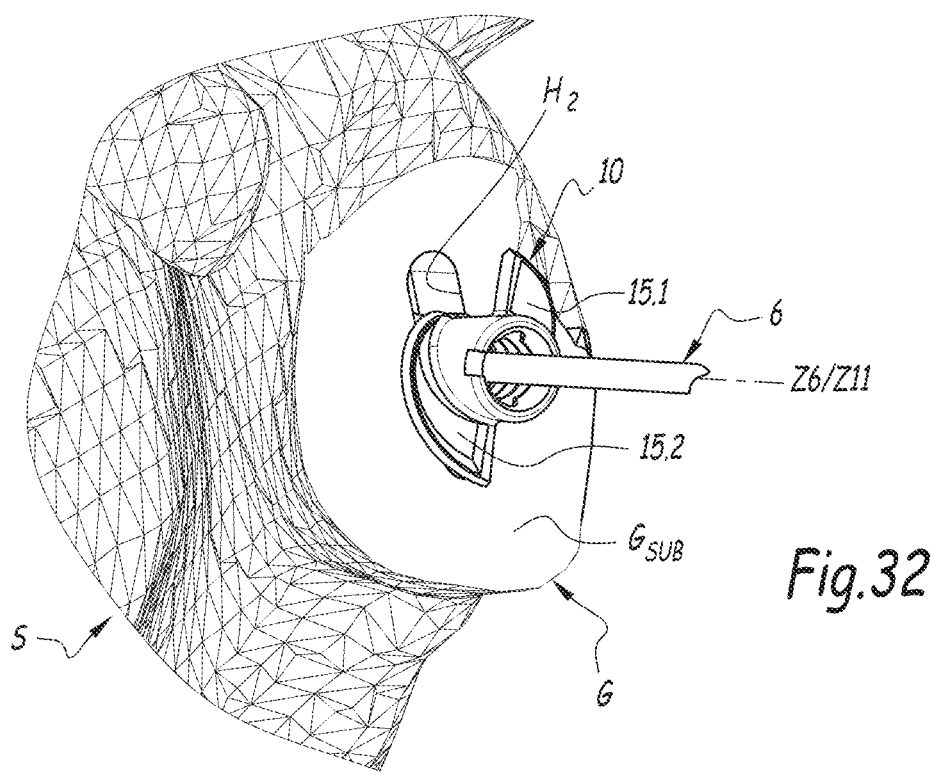

Once the hole H is prepared and while keeping in place the pin 6, the anchorage member 10 is fitted around the pin 6, by substantially aligning the implantation axis Z6 and the axis Z11, as shown in FIG. 31. The anchorage member 10 is then distally translated until the distal end 11B of the body 11 comes into contact with the subchondral bone layer $G_{SUB}$. If necessary, as shown in FIG. 32, the angular position of the anchor member around the axis Z11 is adjusted so that the distal ends 15.1B and 15.2B of the portions of helix 15.1 and 15.2 axially faces the longitudinal slots $H_2$ and $H_3$. At this stage, the body 11 of the anchorage member 10 is arranged above the subchondral bone layer $G_{SUB}$. The anchorage member 10 is then driven in rotation around the axis Z11: each of the portions of helix 15.1 and 15.2 entirely pass through the subchondral bone layer $G_{SUB}$, via the corresponding slot $H_2$, $H_3$. In the same time, the body 11 entirely passes through the subchondral bone layer via the central part $H_1$ of the hole. Indeed, thanks to the lead and the winding of the portions of helix 15.1 and 15.2, rotating the anchorage member 10 drives these portions of helix 15.1 and 15.2 from above to below the subchondral bone layer $G_{SUB}$ and the anchorage member 10 reaches the implantation position shown in the FIGS. 33 to 35. In this implantation position, the proximal ends 15.1A and 15.2A of the portions of helix 15.1 and 15.2 engage underside of the subchondral bone layer $G_{SUB}$, as shown by FIG. 34, whereas the rest of these portions of helix enters spongious bone $G_{SPO}$ of the glenoid G, as shown by FIG. 35. Thus, the thread 15 of the anchorage member 10 has been entirely passed through the subchondral bone layer $G_{SUB}$, from above to below this subchondral bone layer: in the implantation position of the anchorage member 10, the proximal end of the thread, which is formed by the proximal ends 15.1A and 15.2A of the portions of helix 15.1 and 15.2 in the embodiment shown in the figures, engages underside of the subchondral bone layer $G_{SUB}$ and is efficiently retained in place thereby, since this subchondral bone layer has been preserved all around the hole H except at the slots $H_2$ and $H_3$ previously drilled during preparation of the glenoid G. In some embodiments as the one shown in the FIGS. 33 to 35, the implantation of the anchorage member 10 can be thus performed without using cement while benefiting from good mechanical strength.

Referring now to the FIGS. 36 and 37, the anchorage member 10, as in its implantation position of the FIGS. 33 to 35, is completed with other components of the set 1 in order to obtain an anatomic glenoid implant.

FIG. 36 shows that the bone fastening screw 20 is first added to the anchorage member 10, by aligning its axis Z20 with the axis Z11 of the body 11 and by distally introducing first the rod 22 then the head 21 within the inner bore 12 of the body 11. This introduction of the bone fastening screw 20 is performed so that its rod 22 is progressively screwed into cortical bone $G_{COR}$ of the glenoid G, until its head 21 is completely screwed into the threaded hole 19 of the inner bore 12.

FIG. 37 shows that the first insert 50 is then added to the anchorage member 10, by aligning the central axis Z50 of the insert 50 with the axis Z11 of the body 11 and by distally introducing the central peg 52.1 within the inner bore 12 of the body 11. This introduction of the central peg 52.1 is performed so that the coupling feature 52 is fixedly engaged with the first feature 16 of the body 11, especially by fitting along the axis Z11, as shown by the FIG. 37. In practice, the insert 50 can be assembled by being distally impacted. More generally, coupling the anchorage member 10 with the first insert 50 by fitting along the axis Z11 is particularly convenient because the insert 50 is not a component of revolution, which prevents or makes it very complicated any screwing of this insert into the anchoring member already implanted on the glenoid G.

Besides, as shown by FIG. 37, coupling of the first insert 50 with the anchorage member 10 leads to axially introduce the lateral pegs 53 respectively into the slots $H_2$ and $H_3$ of the hole H. The slots $H_2$ and $H_3$ are thus partly plugged by the lateral pegs 53, which improves both stability of the assembly of the anchor member 10 and the insert 50 and healing of the glenoid G.

When the insert 50 is assembled with the anchorage member 10, the distal face 50B of the insert 50 is in direct contact with topside of the subchondral bone layer $G_{SUB}$, as shown by the FIG. 37. This contact can have two interests. Bone colonization of the distal face 50B of the insert 50 can therefore be made possible. And the stresses, which are applied on the insert 50 in use and which have a distal component, are transmitted to the glenoid G at least partly by pressing the distal face 50B of the insert 50 directly against the subchondral bone layer $G_{SUB}$, and not by the anchorage member. The risk of disassembly between the anchorage member and the insert 50 is thus limited.

According to a not shown variant, the second insert 60 is assembled with the anchorage member 10 instead of the first insert 50. In that case, the glenoid G requires additional preparation consisting of drilling free holes in the glenoid so that each of them receives one of the lateral pegs 63 of the insert 60.

According to a not shown variant, the bone fastening screw 20 is not added, which means that the step illustrated by FIG. 36 is omitted.

According to a not shown variant, the spacer 30 and the bone graft 40 can also be added to the anchorage member 10 before assembling one of the inserts 50 and 60 with the anchorage member 10. How adding the spacer 30 and the bone graft 40 to the anchorage member will be explained in detail thereafter.

Whatever the insert selected from the first insert 50 and the second insert 60, the assembly of the anchorage member 10 with the insert, with or without the bone fastening screw 20, and with or without the spacer 30 and the bone graft 40, corresponds to an anatomic glenoid implant.

Referring now to the FIGS. 38 to 42, the anchorage member 10, as in its implantation position of the FIGS. 33 to 35, is completed with other components of the set 1 in order to obtain a reversed glenoid implant.

Figure 38:
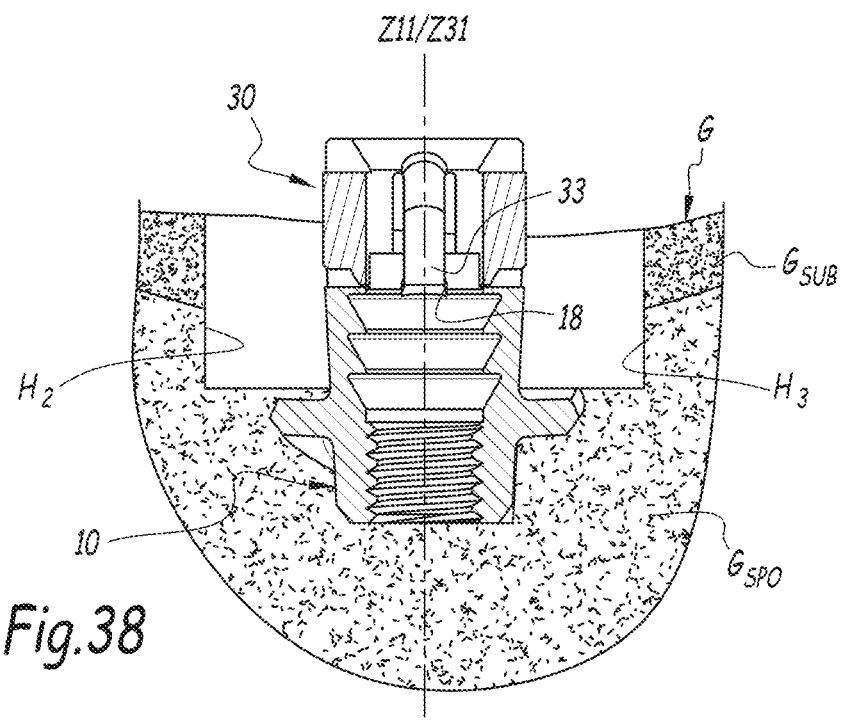

FIG. 38 shows that the spacer 30 is added to the anchorage member 10, by being arranged at the proximal end 11A of the body 11 and by aligning its axis Z31 with the axis Z11 of the body 11. The spacer 30 is distally urged against the body 11 so as to engage its attaching feature 33 with the attaching feature 18 of the body 11, as shown in FIG. 38.

Figure 39:
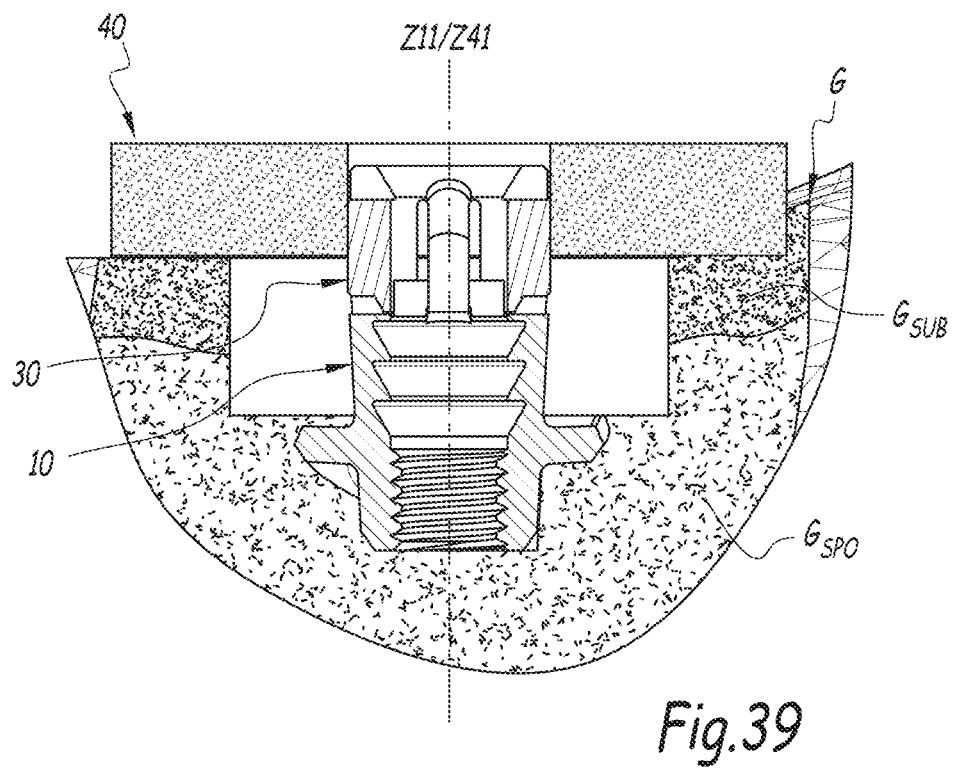

FIG. 39 shows that the bone graft 40 is then added to the anchorage member 10 and the spacer 30, by aligning its axis Z41 with the axis Z11 of the body 11 and by surrounding the spacer 30 with the bone graft 40.

Figure 40:
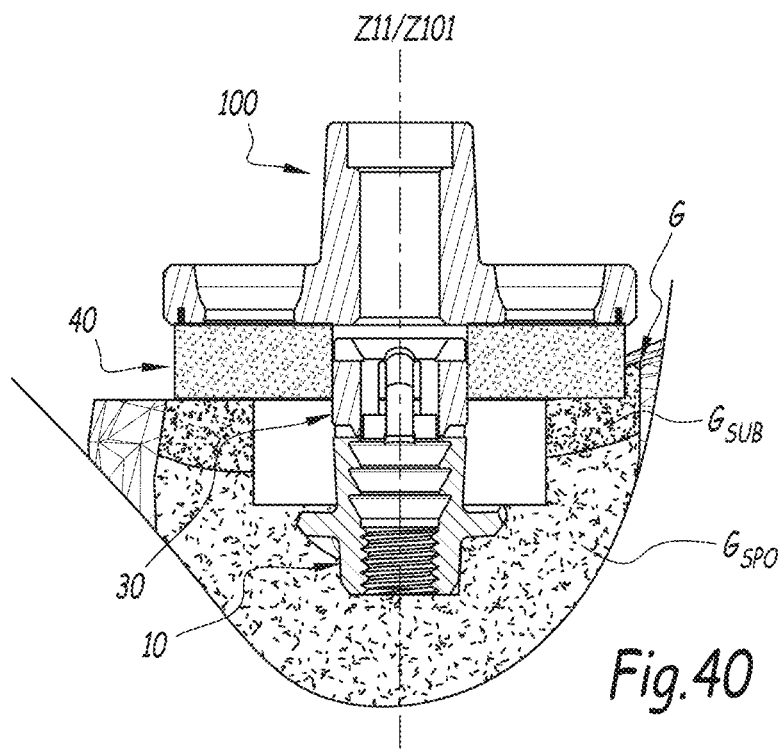

FIG. 40 shows that the second baseplate 100 is added to the anchorage member 10, the spacer 30 and the bone graft 40, by aligning its axis Z101 with the axis Z11 of the body 11 and by arranging the baseplate 100 against the proximal end face 40A of the bone graft 40.

Figure 41:
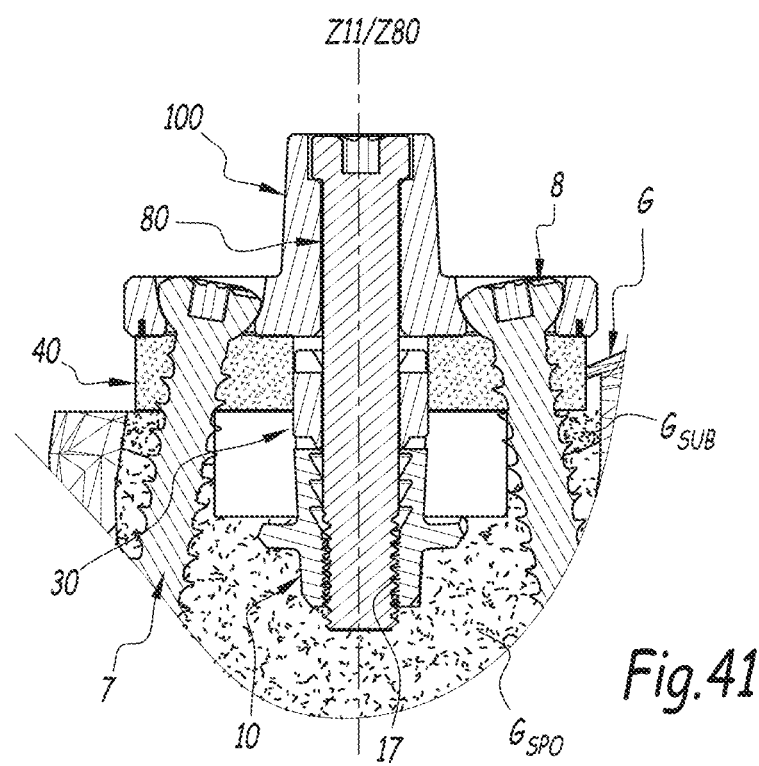

FIG. 41 shows that the second coupling screw 80 is then added to the anchorage member 10, the spacer 30, the bone graft 40 and the baseplate 100, by aligning its axis Z101 with the axis Z11 of the body 11 and by distally introducing the rod 82 then the head 81 within the central bore 102 of the baseplate 100. This introduction of the coupling screw 80 is performed so that its rod 72 is progressively screwed into the second feature 17 of the body, especially the threaded hole 17.1 thereof, until the head 71 is supported against the bearing surface 102.1 of the baseplate 100, as shown in FIG. 41. Moreover, two bone securing screws 7 and 8 are respectively introduced within the lateral through holes 104 of the baseplate 100 so as to be secured into the bone graft 40 and the glenoid G, as shown by FIG. 41.

Figure 42:
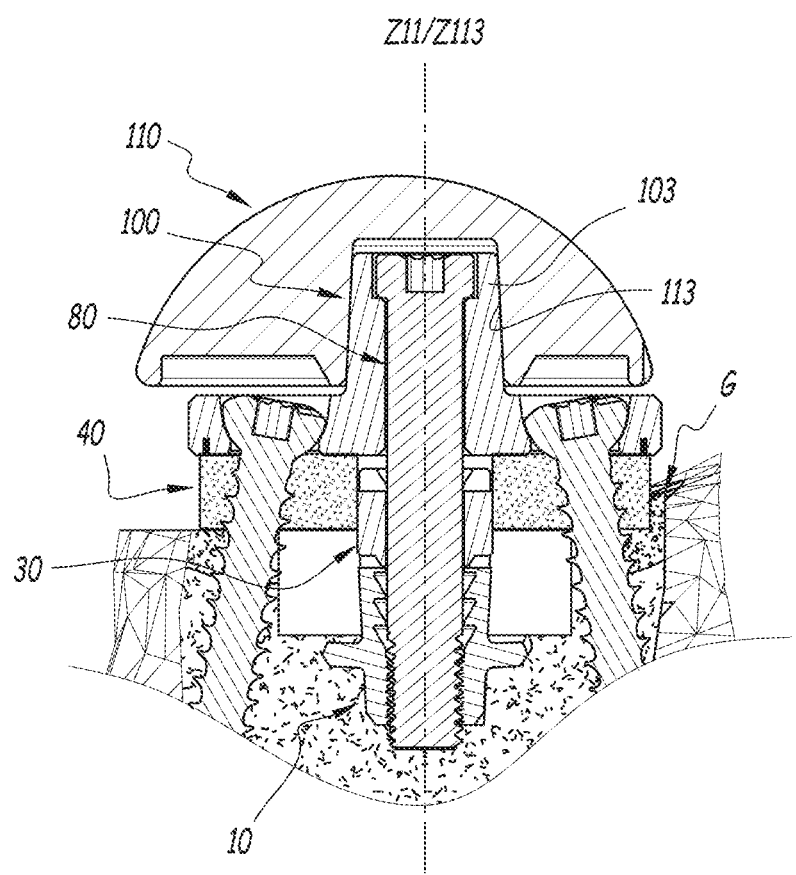

FIG. 42 shows that the first glenosphere 110 is then added to the anchorage member 10, the spacer 30, the bone graft 40, the baseplate 100 and the coupling screw 80, by aligning its connection axis Z113 with the axis Z11 of the body 11 and by arranging the glenosphere 110 at the proximal face 101A of the baseplate 100. The taper connection between the baseplate 100 and the glenosphere 110 is then carried out by engaging the male part 103 into the female part 113, as shown by FIG. 42.

According to another not shown variant, the second glenosphere 120 is added instead of the first glenosphere 110.

According to a not shown variant, the spacer 30 and the bone graft 40 are not added to the anchorage member, which means that the steps illustrated by the FIGS. 38 and 39 are omitted. In that case, the distal face 101B of the baseplate 100 is put in contact directly with the glenoid G. Also in that case, the first coupling screw 70 is used instead of the second coupling screw 80.

According to another not shown variant, the first baseplate 90 is assembled with the anchorage member 10, instead of the second baseplate 100. Using the first baseplate 90 can be preferred when the bone graft 40 is not used, so that the convex distal face 91B of the body 91 of the baseplate 90 matches the glenoid G, or when the proximal end face 40A of the bone graft is concave shaped.

According to another not shown variant, the taper connection between the baseplate 90, 100 and the glenosphere 110, 120 may be reversed. In that case, a male part of this taper connection is provided on the glenosphere and a female part of the taper connection is provided on the baseplate.

Whatever the baseplate selected from the baseplate 90 and 100, whatever the glenosphere selected from the glenospheres 110 and 120, and whatever the coupling screw selected from the coupling screws 70 and 80 depending on whether the spacer 30 and the bone graft 40 are used, the assembly of the anchorage member 10 with the baseplate, the glenosphere and the coupling screw and with or without the spacer 30 and the bone graft 40 corresponds to a reversed glenoid implant.

Based on the foregoing, it will be understood that while the anchorage member 10 is already implanted, this anchorage member can be used as well in the anatomic glenoid implant than in the reversed glenoid implant, thanks to its first feature 16 and second feature 17 allowing the body 11 to be coupled indifferently with one or with the other of the anatomic articulating member AAM and the reversed articulating member RAM. Choosing to implant the anatomic glenoid implant or the reversed glenoid implant can thus be delayed until surgery, after having implanted the anchorage member. It makes also possible to easily convert a previously implanted anatomic glenoid implant into a reversed glenoid implant while keeping the anchorage member.

In some not shown embodiments, the spacer can be integral with the body of the anchorage member when it is certain that the bone graft will be used in the glenoid implant to be obtained from the set.

In some not shown embodiments, a part, especially the male part, of the taper connection by which the glenosphere is fixedly mounted on the baseplate, can be integral with the body of the anchorage member. In that case, the use of the set is limited to exclusively obtain a reversed glenoid implant and coupling the anchorage member with the baseplate by an added coupling screw is not necessary. Therefore, any insert as the inserts 50 and 60 and any coupling screw as the screws 70 and 80 can be omitted in the corresponding set.

The invention claimed is:
1. A set for a glenoid implant, comprising:
an anatomic articulating member, including a concave articulating surface configured to articulate with a complementary humeral implant,
a reversed articulating member, including a convex articulating surface configured to articulate with a complementary humeral implant, and
an anchorage member configured to be anchored in a human glenoid, the anchorage member including a body, which defines a proximodistal axis, that is operable to be axially introduced into the glenoid before being coupled with one or the other of the anatomic and reversed articulating members, wherein the body includes an inner bore extending along the proximodistal axis, the inner bore including a threaded hole that is centered on the proximodistal axis, and an outer thread that is configured such that when the body is driven in rotation around the proximodistal axis so as to be introduced into the glenoid, the outer thread passes through a subchondrial bone layer of the glenoid, the outer thread including at least one portion of helix which has a lead between twelve and eighteen millimeters and wraps around the body less than one turn and more than half of one turn, the reversed articulating member includes:
  a baseplate including a proximal face and a distal face,
  a glenosphere including the convex articulating surface, the glenosophere fixedly mounted on the proximal face of the baseplate, and
  a coupling screw, which is separate from the baseplate and which is configured to fixedly couple the anchorage member with the baseplate, the coupling screw including:
    a threaded rod which is configured to protrude from the distal face of the baseplate and is configured to be coupled to a thread of the threaded hole when the threaded rod is received through the baseplate and introduced within the inner bore, and
    a head which is configured to be axially retained against the baseplate in a distal direction when the threaded rod is screwed into the threaded hole in the distal direction, the anatomic articulating member includes an anatomic coupling feature that is shaped differently from the threaded rod, and the inner bore of the body further includes an inner feature that is distinct from the threaded hole and that is configured to cooperate with the anatomic coupling feature when the anatomic coupling feature is introduced within the inner bore to fixedly couple the anchorage member with the anatomic articulating member.

2. The set according to claim 1, wherein the inner feature and the threaded hole are located at respective axial levels of the body that are different from each other.

3. The set according to claim 1, wherein the anatomic coupling feature and the inner feature cooperate with each other by fitting along the proximodistal axis.

4. The set according to claim 3, wherein the anatomic coupling feature and the inner feature are fitted together by snap fit along the proximodistal axis.

5. The set according to claim 4, wherein the inner feature comprises a corrugated hole that is centered on the proximodistal axis, and
  wherein the anatomic coupling feature comprises a peg that is integral with an insert of the anatomic articulating member and that is shaped to be axially received and to be wedged in the corrugated hole.

6. The set according to claim 1, wherein the anatomic articulated member comprises an insert having a proximal face, on which is formed the concave articulating surface, and a distal face, from which at least a part of the anatomical coupling feature protrudes.

7. The set according to claim 1, wherein the glenosphere is fixedly mounted on the baseplate by a taper connection that is centered on the proximodistal axis.

8. The set according to claim 1, wherein the glenosphere defines a central axis which is both parallel to the proximodistal axis and offset from the proximodistal axis when the reversed articulating member is coupled with the anchorage member.

9. The set according to claim 1, wherein the outer thread of the body is configured to pass through the subchondral bone layer of the glenoid by entirely passing from above to below the subchondral bone layer so that a proximal end of the thread engages an underside of the subchondral bone layer and the remainder of the outer thread enters spongious bone of the glenoid when the body is driven in rotation around the proximodistal axis while being introduced into the glenoid.

10. The set according to claim 1, wherein the set further comprises a bone fastening screw configured to be screwed into cortical bone of the glenoid, the bone fastening screw being operable to be axially passed through the body so that a threaded rod of the bone fastening screw protrudes axially from the body so as to be screwed into cortical bone of the glenoid while a threaded head of the bone fastening screw is screwed in a complementary threaded distal hole of the body.

11. The set according to claim 1, wherein the baseplate is provided with a bearing surface against which the head of the coupling screw is axially supported in the distal direction.

12. A set for a glenoid implant, comprising:
  an anatomic articulating member, including a concave articulating surface configured to articulate with a complementary humeral implant,
  a reversed articulating member, including a convex articulating surface configured to articulate with a complementary humeral implant, and
  an anchorage member configured to be anchored in a human glenoid, the anchorage member including a body, which defines a proximodistal axis, that is operable to be axially introduced into the glenoid before being coupled with one or the other of the anatomic and reversed articulating members, wherein
  the body includes an inner bore extending along the proximodistal axis, the inner bore including a threaded hole that is centered on the proximodistal axis, and an outer thread that is configured to pass through a subchondral bone layer of the glenoid when the body is driven in rotation around the proximodistal axis while being introduced into the glenoid,
  the reversed articulating member includes:
    a baseplate including a proximal face and a distal face,
    a glenosphere including the convex articulating surface, the glenosophere fixedly mounted on the proximal face of the baseplate, and
    a coupling screw, which is separate from the baseplate and which is configured to fixedly couple the anchorage member with the baseplate, the coupling screw including:
      a threaded rod which is configured to protrude from the distal face of the baseplate and is configured to be screwed into coupled to a thread of the threaded hole when the threaded rod is received through the baseplate and introduced within the inner bore, and
      a head which is configured to be axially retained against the baseplate in a distal direction when the threaded rod is screwed into the threaded hole in the distal direction,
  the anatomic articulating member includes an anatomic coupling feature that is shaped differently from the threaded rod, and the inner bore of the body further includes an inner feature that is distinct from the threaded hole and that is configured to cooperate with the anatomic coupling feature when the anatomic coupling feature is introduced within the inner bore to fixedly couple the anchorage member with the anatomic articulating member, and wherein the outer thread including at least one portion of a helix which includes a lead between twelve and eighteen millimeters and wraps around the body less than one turn and more than half of one turn.

13. The set according to claim 12, wherein the inner feature and the threaded hole are located at respective axial levels of the body that are different from each other.

14. The set according to claim 12, wherein the anatomic coupling feature and the inner feature cooperate with each other by fitting along the proximodistal axis.

15. The set according to claim 12, wherein the anatomic coupling feature and the inner feature are fitted together by snap fit along the proximodistal axis.

16. A glenoid implant, comprising:
an articulating member configured to articulate with a humeral implant, and
an anchorage member configured to be anchored in a human glenoid, the anchorage member including a body, which defines a proximodistal axis, that is operable to be axially introduced into the glenoid before being fixedly coupled with the articulating member, wherein
the body includes an outer face that is cylindrical or frustoconical and convergent towards a distal end of the body, and a thread that outwardly protrudes from the outer face and is configured to pass through a subchondral bone layer of the glenoid by entirely passing from above to below the subchondral bone layer so that a proximal end of the thread engages an underside of the subchondral bone layer and the remainder of the thread enters spongious bone of the glenoid when the body is driven in rotation around the proximodistal axis while being introduced into the glenoid, and
the thread includes a helix that has a proximal end defining a proximal end of the thread and is configured to entirely pass through the subchondral bone layer via a longitudinal slot of the subchondral bone layer when the body is driven in rotation around the proximodistal axis while being introduced into the glenoid, wherein the helix wraps around the body less than one turn and more than half of one turn and the helix includes a lead between twelve and eighteen millimeters.

17. The glenoid implant according to claim 16, wherein the helix has a width which gradually decreases from its proximal end to its distal end.

18. The glenoid implant according to claim 16, wherein the proximal end of the thread has a width that is greater than the remainder of the thread.

19. A glenoid implant, comprising:
an articulating member configured to articulate with a humeral implant, and
an anchorage member configured to be anchored in a human glenoid, the anchorage member including a body which defines a proximodistal axis and which is operable to be axially introduced into the glenoid before being fixedly coupled with the articulating member,
the body is provided with an outer thread which is configured such that when the body is driven in rotation around the proximodistal axis so as to be introduced into the glenoid, the outer thread passes through a subchondral bone layer of the glenoid, the outer thread including at least one portion of helix which has a lead between twelve and eighteen millimeters and wraps around the body less than one turn and more than half of one turn.

20. The glenoid implant according to claim 19, wherein the at least one portion of helix has a width which gradually decreases from its proximal end to its distal end.

* * * * *